(12) United States Patent
Jeong et al.

(10) Patent No.: US 11,260,143 B2
(45) Date of Patent: Mar. 1, 2022

(54) AIR PURIFIER

(71) Applicant: Seoul Viosys Co., Ltd., Ansan-si (KR)

(72) Inventors: Woong Ki Jeong, Ansan-si (KR); Sang Wook Jung, Ansan-si (KR); Jong Rack Kim, Ansan-si (KR); Si Ho Yu, Ansan-si (KR); Hee Cheul Jung, Ansan-si (KR); Byung Chul Joo, Ansan-si (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 48 days.

(21) Appl. No.: 16/462,865

(22) PCT Filed: Nov. 20, 2017

(86) PCT No.: PCT/KR2017/013191
§ 371 (c)(1),
(2) Date: May 21, 2019

(87) PCT Pub. No.: WO2018/097560
PCT Pub. Date: May 31, 2018

(65) Prior Publication Data
US 2020/0061231 A1    Feb. 27, 2020

(30) Foreign Application Priority Data

Nov. 22, 2016  (KR) .................. 10-2016-0155968
Jan. 2, 2017   (KR) .................. 10-2017-0000352

(51) Int. Cl.
*A61L 9/20*     (2006.01)
*B01D 46/42*    (2006.01)
(Continued)

(52) U.S. Cl.
CPC .............. *A61L 9/20* (2013.01); *B01D 46/42* (2013.01); *A61L 2209/14* (2013.01);
(Continued)

(58) Field of Classification Search
CPC ........ A61L 9/20; A61L 9/205; A61L 2209/14; B01D 46/42; B01D 46/0005;
(Continued)

(56) References Cited

U.S. PATENT DOCUMENTS 7,166,259 B2 *  1/2007  Beam ................... A61L 9/22
                                              422/186.04
10,215,433 B2 *  2/2019  Lee .................... F24F 13/28
(Continued)

FOREIGN PATENT DOCUMENTS

JP    2005-036701      2/2005
KR    10-2004-0021336  3/2004
(Continued)

OTHER PUBLICATIONS

International Search Report dated Mar. 8, 2018, issued in International Application No. PCT/KR2017/013191.

*Primary Examiner* — Regina M Yoo
(74) *Attorney, Agent, or Firm* — H.C. Park & Associates, PLC

(57) ABSTRACT

An air purifier including a body including a suction port and a discharge port disposed on opposing surfaces thereof, and having an inner space through which air flows from the suction port to the discharge port, a fan disposed in the inner space and having a side surface separated from an inner wall of the body, at least one light source module disposed in the inner space to emit UV light, a power controller mounted on the inner wall and connected to a power source to supply electric power to the light source module, a cover mounted on the inner wall to cover the power controller, and at least one filter disposed in the inner space of the body, in which the cover includes a tilted air flow guide facet to guide tilted to allow air suctioned through the suction port toward the filter.

9 Claims, 27 Drawing Sheets

(51) Int. Cl.
  *B01D 46/00* (2022.01)
  *B01J 35/00* (2006.01)
  *F24F 13/20* (2006.01)
  *F24F 8/22* (2021.01)

(52) U.S. Cl.
  CPC ......... *B01D 46/0005* (2013.01); *B01J 35/004* (2013.01); *F24F 8/22* (2021.01); *F24F 13/20* (2013.01)

(58) Field of Classification Search
  CPC ................ B01D 46/0004; B01D 46/46; B01D 46/0028; B01D 46/0024; B01D 2273/30; B01D 46/0009; F24F 8/22; F24F 13/20; F24F 11/49; F24F 3/16; F24F 13/28; B01J 35/004; F21V 33/00

See application file for complete search history.

(56) References Cited

U.S. PATENT DOCUMENTS

| | | | |
|---|---|---|---|
| 10,517,980 B2* | 12/2019 | Kim | B01D 53/885 |
| 10,871,295 B2* | 12/2020 | Kim | F24F 8/10 |
| 10,918,760 B2* | 2/2021 | Jeong | F25D 17/06 |
| 2002/0098127 A1* | 7/2002 | Bollini | A61L 9/20 |
| | | | 422/121 |
| 2005/0163648 A1* | 7/2005 | Liang | A61L 2/10 |
| | | | 422/1 |
| 2006/0008391 A1* | 1/2006 | Yuen | A61L 9/122 |
| | | | 422/120 |
| 2006/0086138 A1* | 4/2006 | Park | F24F 1/005 |
| | | | 62/428 |
| 2017/0122601 A1* | 5/2017 | Lee | F24F 11/30 |
| 2019/0134251 A1* | 5/2019 | Jeong | F25D 17/042 |

FOREIGN PATENT DOCUMENTS

| | | |
|---|---|---|
| KR | 10-0645904 | 11/2006 |
| KR | 10-0834585 | 6/2008 |
| KR | 10-2012-0072722 | 7/2012 |

* cited by examiner

AIR PURIFIER

CROSS REFERENCE TO RELATED APPLICATIONS

This application is the National Stage Entry of International Patent Application No. PCT/KR2017/013191, filed on Nov. 20, 2017, and claims priority from and the benefit of Korean Patent Application No. 10-2016-0155968, filed on Nov. 22, 2016 and Korean Patent Application No. 10-2017-0000352, filed on Jan. 2, 2017, each of which is incorporated by reference for all purposes as if fully set forth herein.

FIELD

Exemplary embodiments of the disclosure relate generally to an air purifier.

DISCUSSION OF THE BACKGROUND

Generally, an air purifier uses a blower, such as a fan, to circulate air through various filters, such as a prefilter, a deodorizing filter, and a HEPA filter, to remove pollutants including fine dust, bacteria, and volatile organic compounds (VOCs) such as formaldehyde from the air.

Recently, as it has been known that air pollutants can be released from furniture, office supplies, home appliances, interior paints on new houses, interior goods, automobile interior materials, toilets, and the like, there is a growing interest in indoor air quality. Accordingly, there is an increasing demand for a small air purifier, which is easy to install, simple to use, and does not take up much space, which may be suitable for use in houses, offices, automobiles, and the like.

The recent development of semiconductor technology has enabled high efficiency ultraviolet (UV) light emitting diodes to be produced at lower costs. As such, photocatalytic filters are widely used as deodorizing filters. A photocatalytic filter is fabricated by coating an air-permeable material, such as metal foam or porous metal, with a photocatalytic material, such as $TiO_2$, $ZnO$, $ZrO_2$, or $WO_3$, and can generate hydroxyl radicals to decompose contaminants or odorous substances when irradiated with UV light. Such a photocatalytic filter can be reused through cleaning after a certain period of the usage.

However, a typical small air purifier has a structure that makes it difficult to disassemble a case for removing a reusable filter, such as a deodorizing filter or a prefilter, from the air purifier. Therefore, there is a need for an air purifier that allows easy replacement and attachment/detachment of a filter.

In addition, the HEPA filter is configured to collect fine dust in air. Thus, the fine dust collected from air adheres to the HEPA filter. In this case, microorganisms such as virus and bacteria contained in the fine dust remain on the HEPA filter, and thus are left inside the air purifier.

SUMMARY

It is one aspect of the exemplary embodiments to provide an air purifier that allows easy attachment/detachment of a filter upon replacement of the filter in the air purifier.

It is another aspect of the exemplary embodiments to provide an air purifier that includes a cover capable of protecting a power controller disposed inside the air purifier from external impact or from contact with other components inside the air purifier.

It is a further aspect of the exemplary embodiments to provide an air purifier that can sterilize microorganisms adhered to a HEPA filter.

In accordance with one exemplary embodiment, an air purifier including a body, a fan, at least one light source module, a power controller, and a cover is provided. The body is formed on one surface thereof with a suction port and on the other surface thereof with a discharge port, is provided with a power source, and has an inner space through which air flows from the suction port to the discharge port. The fan is disposed in the inner space of the body. The at least one light source module is disposed in the inner space of the body and emits UV light. The power controller is mounted on an inner wall of the body and is physically or electrically connected to the power source to supply power to the light source module. The cover is mounted on the inner wall of the body and is formed to cover the power controller.

In accordance with another exemplary embodiment, an air purifier including a body, a fan, at least one filter, at least one light source module, and a door is provided. The body is formed with a suction port, a discharge port, and a filter replacement portion having an opening shape, and has an inner space through which air flows from the suction port to the discharge port. The fan is disposed in the inner space of the body. The at least one filter is disposed in the inner space of the body. The at least one light source module emits UV light toward the filter. The door is mounted on an outer wall of the body to open or close the filter replacement portion. Here, the filter is detachably attached to an interior of the body through the filter replacement portion.

According to an exemplary embodiment, the air purifier may be provided with a door to allow replacement of a filter without dissembling the air purifier.

According to an exemplary embodiment, the air purifier may be provided with a cover surrounding a power controller to prevent failure of the power controller due to external impact or contact with other components thereof.

According to an exemplary embodiment, the air purifier may be adapted to sterilize microorganisms adhered to a HEPA filter, thereby improving air purification performance.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
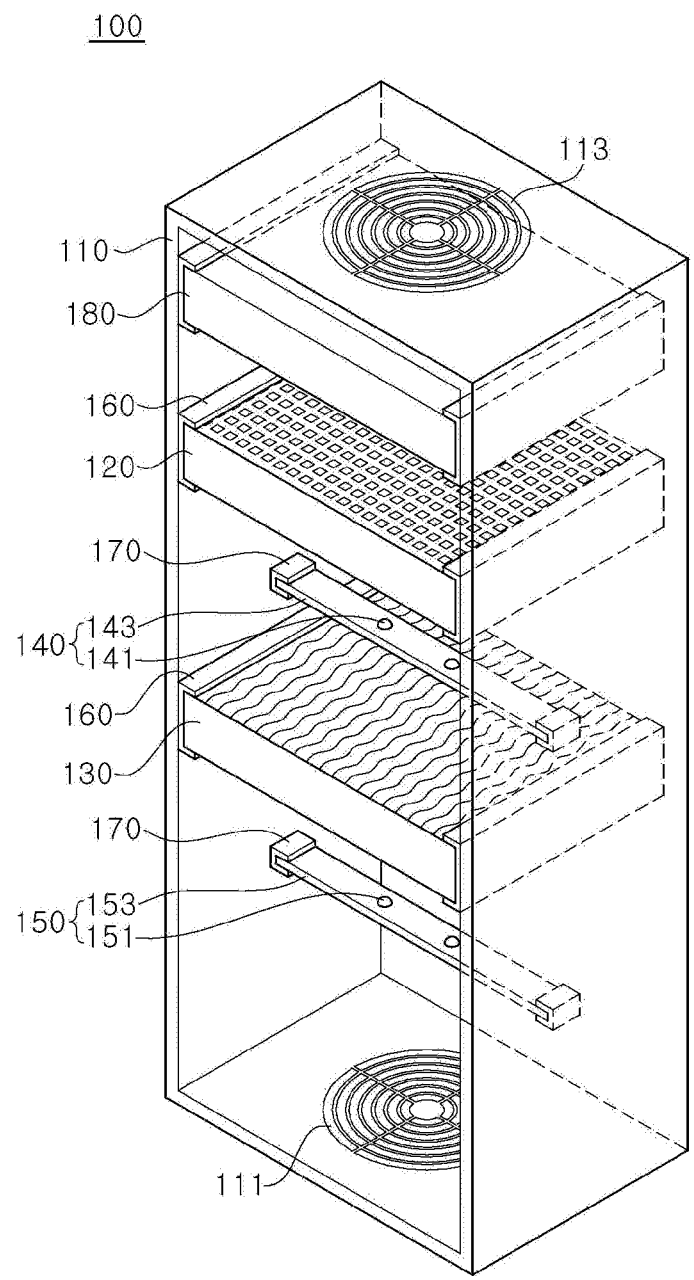
FIG. 1 is a schematic view of an air purifier according to a first exemplary embodiment.

Hereinafter, embodiments of the present disclosure will be described in detail with reference to the accompanying drawings. It should be understood that the following embodiments are provided for complete disclosure and thorough understanding of the invention by those skilled in the art. Therefore, the exemplary embodiment of the disclosure is not limited to the following embodiments and may be embodied in different ways. In addition, widths, lengths, thicknesses, and the like of elements can be exaggerated for clarity and descriptive purposes. When an element or component is referred to as being "on," "connected to," or "coupled to" another element or component, it may be directly on, connected to, or coupled to the other element or layer or intervening elements or components may be present therebetween. In addition, spatially relative terms, such as "upper surface," "lower surface," "rear surface," "front surface," and the like, may be used herein for descriptive purposes and do not restrict a direction in which an element or component is formed. Like reference numerals denote like elements throughout the specification.

According to an exemplary embodiment, an air purifier includes a body, a fan, at least one light source module, a power controller, and a cover. The body is formed on one surface thereof with a suction port and on the other surface thereof with a discharge port, is provided with a power source, and has an inner space through which air flows from the suction port to the discharge port. The fan is disposed in the inner space of the body. The at least one light source module is disposed in the inner space of the body and emits UV light. The power controller is mounted on an inner wall of the body and is physically or electrically connected to the power source to supply electric power to the light source module. The cover is mounted on the inner wall of the body and is formed to cover the power controller.

The light source module may emit the UV light toward air flowing in the inner space of the body.

The body may be further formed at both sides thereof with filter securing portions disposed on the inner wall thereof to receive both sides of the filter inserted thereinto.

The fan may be secured to one side of the cover.

The body may be further formed with a fan securing portion disposed at one side of the cover to be parallel to the discharge port and securing the fan.

The fan secured to the fan securing portion may have a side surface separated from the inner wall of the body.

The cover may further include a light source module support. The light source module support may support the light source module to be separated from the cover.

The body may be further formed with light source module grooves disposed on the inner wall thereof to receive both sides of the light source module inserted thereinto.

The air purifier may further include at least one filter disposed in the inner space of the body.

The at least one filter may include at least one of a photocatalytic filter and a HEPA filter.

The at least one light source module may emit UV light toward the photocatalytic filter or the HEPA filter, or may include two light source modules, one of which emits UV light toward the photocatalytic filter and the other of which emits UV light toward the HEPA filter.

The cover may be formed at the other side thereof with an air flow guide facet tilted to allow air suctioned through the suction port to flow toward the filter.

The air flow guide facet may be tilted to have a gradually increasing height from the suction port toward the filter.

The air purifier may further include a resilient frame disposed to surround an outer surface of the filter.

According to another exemplary embodiment, an air purifier includes a body, a fan, at least one filter, at least one light source module, and a door. The body is formed with a suction port, a discharge port, and a filter replacement portion having an opening shape, and has an inner space through which air flows from the suction port to the discharge port. The fan is disposed in the inner space of the body. The at least one filter is disposed in the inner space of the body. The at least one light source module emits UV light toward the filter. The door is mounted on an outer wall of the body to open or close the filter replacement portion. Here, the filter is detachably attached to an interior of the body through the filter replacement portion.

The body may be further formed at both sides thereof with groove-shaped filter securing portions disposed on an inner wall thereof to receive both sides of the filter inserted thereinto.

The filter securing portions may extend to the filter replacement portion. Both sides of each of the filter replacement portions have a groove structure depressed along the filter securing portions.

The body may be further formed with light source module grooves disposed on the inner wall thereof to receive both sides of the light source module inserted thereinto.

The air purifier may further include a resilient frame disposed to surround an outer surface of the filter.

The air purifier may further include stoppers protruding to face each other at both sides of an inlet of the filter replacement portion.

The at least one filter may include at least one of a photocatalytic filter and a HEPA filter.

The at least one light source module may emit UV light toward the photocatalytic filter or the HEPA filter, or may include two light source modules, one of which emits UV light toward the photocatalytic filter and the other of which emits UV light toward the HEPA filter.

The air purifier may further include: door guides formed at both sides of the door to continuously protrude from an inner wall of the door; and door guide grooves formed on an outer wall of the body so as to correspond to the door guides.

The door guides are inserted into the door guide grooves when the door closes the filter replacement portion.

The air purifier may further include: a door securing portion formed at one end of each of the door guides to protrude outwards; and a door securing groove formed at one end of each of the door guide grooves so as to correspond to the door securing portion. The door securing portions are inserted into the door securing grooves when the door closes the filter replacement portion.

According to a further exemplary embodiment, an air purifier includes a body, at least one light source module, a cover, a fan securing portion, and a fan. The body is formed on one surface thereof with a suction port and on the other surface thereof with a discharge port, is provided with a power source, and has an inner space through which air flows from the suction port to the discharge port. The at least one light source module is disposed in the inner space of the body and emits UV light. The cover is mounted on the inner wall of the body. The fan securing portion is formed at one side of the cover to be perpendicular to the inner wall of the body on which the cover is mounted. The fan is secured to the fan securing portion. Here, the fan secured to the fan securing portion is separated from the inner wall of the body.

Hereinafter, exemplary embodiments of the present disclosure will be described in detail with reference to the accompanying drawings.

FIG. 1 is a schematic view of an air purifier according to a first exemplary embodiment.

Referring to FIG. 1, an air purifier 100 includes a body 110, a photocatalytic filter 120, a HEPA filter 130, a first light source module 140, and a second light source module 150. The air purifier 100 further includes well-known components, such as a fan 180, and thus, detailed descriptions as to the well-known components will be omitted. Referring to FIG. 1, the fan 180 is disposed between a discharge port 113 and a photocatalytic filter 120. However, the inventive concepts are not limited thereto, and in some exemplary embodiments, the fan 180 may be disposed at any locations inside or outside the air purifier 100.

The body 110 is formed with a suction port 111 and the discharge port 113 on an outer wall thereof. The suction port 111 refers to an opening through which external air is suctioned into an inner space of the body 110. The discharge port 113 refers to an opening through which air is discharged to the outside after being subjected to sterilization and purification inside the body 110. The suction port 111 and the discharge port 113 are formed on different surfaces of the body 110.

In the inner space of the body 110, the photocatalytic filter 120, the HEPA filter 130, the first light source module 140, and the second light source module 150 are sequentially arranged. In addition, the photocatalytic filter 120, the HEPA filter 130, the first light source module 140, and the second light source module 150 are disposed between the suction port 111 and the discharge port 113.

The body 110 is formed on the inner wall thereof with filter securing portions 160 and light source module securing portions 170. The filter securing portions 160 may secure filters, such as the photocatalytic filter 120 and the HEPA filter 130, inside the body 110. In addition, the light source module securing portions 170 may secure the first light source module 140 and the second light source module 150 inside the body 110. For example, the light source module securing portions 170 may be formed to secure the first light source module 140 and the second light source module 150 along a central line on one surface of each of the photocatalytic filter 120 and the HEPA filter 130.

In the illustrated exemplary embodiment, both sides of each of the photocatalytic filter 120, the HEPA filter 130, the first light source module 140, and the second light source module 150 are inserted into the filter securing portions 160 or the light source module securing portions 170 to be secured to the body 110. However, the inventive concepts are not limited thereto, and in some exemplary embodiments, the structure for securing the photocatalytic filter 120, the HEPA filter 130, the first light source module 140, and the second light source module 150 inside the body 110 may be variously modified.

The body 110 may be formed of metal or a resin material, such as a plastic material. Further, the body 110 may be formed in any structure including a rectangular column shape, a circular column shape, or a conical shape, so long as the body 110 has an inner space.

Referring to FIG. 1, the second light source module 150, the HEPA filter 130, the first light source module 140, and the photocatalytic filter 120 are sequentially arranged in a direction from the suction port 111 to the discharge port 113.

The photocatalytic filter 120 is formed by coating a photocatalytic material on a base having a plurality of through holes. The base of the photocatalytic filter 120 is formed of a porous ceramic material. Alternatively, the base may be formed of a metal foam material including nickel (Ni), iron (Fe), aluminum (Al), chromium (Cr), and the like. A surface of the base is coated with the photocatalytic material. The photocatalytic material includes at least one selected from among $TiO_2$, $ZnO$, $ZrO_2$, and $WO_3$. Alternatively, the photocatalytic filter 120 may be made of a photocatalytic material.

The first light source module 140 includes first light sources 141 and a first light source substrate 143. The first light sources 141 are mounted on one surface of the first light source substrate 143. The first light source module 140 is disposed such that the first light sources 141 face the photocatalytic filter 120 to emit UV light toward the photocatalytic filter 120. For example, UV light emitted from the first light source module 140 may be UVA having a wavelength in the range of 315 nm to 400 nm.

UV light emitted from the first light source module 140 reacts with the photocatalytic material of the photocatalytic filter 120 to form hydroxyl radicals (·OH). The generated hydroxyl radicals remove pollutants or odorous substances through decomposition. In this manner, the air is purified by such photocatalytic reaction while passing through the through holes of the photocatalytic filter 120.

The photocatalytic filter 120 may react to a plurality of ultraviolet wavelengths. If the photocatalytic filter 120 reacts to multiple wavelengths, the range of wavelengths irradiated to the photocatalytic filter 120 is broadened. As the photocatalytic filter 120 responds to a wide range of ultraviolet wavelengths, air purification performance of the air purifier 100 can be improved.

The HEPA filter 130 may collect fine dusts in air. Fine dusts having minute particle sizes are harmful to the human body, since such particles cannot be filtered by the upper respiratory systems, such as nose and bronchial tubes. Since the HEPA filter 130 collects fine dusts harmful to the human body, air having passed through the HEPA filter 130 may be free from fine dusts. However, in the HEPA filter 130, the collected fine dusts adhere to an air inlet side thereof. Microorganisms such as bacteria and viruses are present in the fine dust. Therefore, various microorganisms may be present on the surface of the HEPA filter 130 together with the collected fine dusts.

The second light source module 150 includes second light sources 151 and a second light source substrate 153. The second light sources 151 are mounted on one surface of the second light source substrate 153 to face the HEPA filter 130. The second light source module 150 emits UV light toward the HEPA filter 130. A UV light emission direction of the second light source module 150 is a direction of air flowing into the HEPA filter 130. That is, a portion of the HEPA filter 130 irradiated with UV light is an air inflow surface thereof. For example, UV light emitted from the second light source module 150 is UVC having a wavelength in the range of 200 nm to 290 nm.

The second light source module 150 sterilizes the HEPA filter 130 by emitting UV light to the HEPA filter 130. More specifically, the second light source module 150 sterilizes microorganisms in the fine dust adhered to one side of the HEPA filter 130. Since the second light source module 150 is disposed to face one side of the HEPA filter 130, microorganisms adhered to the one side of the HEPA filter 130 are directly irradiated with UV light from the second light source module 150. As such, the air purifier has improved sterilization efficiency. In this way, since the microorganisms in the fine dust are removed by sterilizing the HEPA filter 130, the air purifier 100 can prevent the microorganisms from passing through the HEPA filter 130 and moving together with the air flow.

In addition, since the second light source module 150 is disposed to face the one side of the HEPA filter 130, air is sterilized by UV light emitted from the second light source module 150 during movement of the air between the second light source module 150 and the HEPA filter 130. As such, the microorganisms are exposed to UV light not only when the microorganisms are attached to one side of the HEPA filter 130 but also when the microorganisms move together with the air. In this manner, the time during which the microorganism are exposed to UV light is increased, thereby improving sterilization efficiency.

Accordingly, air having passed through the HEPA filter 130 is an air free from both of fine dust and microorganisms. As such, air flowing into the photocatalytic filter 120 is free from the microorganisms. Since the air free from the microorganisms passes through the photocatalytic filter 120, the air purifier 100 can prevent the photocatalytic filter 120 from being contaminated by microorganisms in the air. That is, since the air purifier 100 can prevent the photocatalytic filter 120 from being contaminated by air, the air purifier 100 can prevent deterioration in deodorization and sterilization effects with respect to the photocatalytic filter 120. As a result, it is possible to prevent deterioration in air purification efficiency of the air purifier 100.

The HEPA filter 130 has a structure in which a plurality of filter layers overlap each other. A fraction of UV light emitted from the second light source module 150 passes through a gap between the filter layers of the HEPA filter 130. The microorganisms may be collected between the filter layers. Here, when UV light emitted from the second light source module 150 passes through the filter layers, the microorganisms collected between the filter layers can be sterilized thereby. In addition, the microorganisms having passed through the HEPA filter 130 together with air can be sterilized through continuous irradiation with UV light emitted from the second light source module 150 and having passed through the HEPA filter 130. In this manner, sterilization efficiency of the air purifier 100 can be increased through continuous emission of UV light from the second light source module 150.

UV light emitted from the second light source module 150 and having passed through the HEPA filter 130 reaches the photocatalytic filter 120. Accordingly, the photocatalytic filter 120 is subjected to photocatalytic reaction by the UV light emitted from the first light source module 140 and a fraction of the UV light emitted from the second light source module 150. That is, since the photocatalytic filter 120 is subjected to photocatalytic reaction with higher intensity of UV light than the intensity of the UV light emitted from the first light source module 140, the air purifier 100 according to the illustrated exemplary embodiment has improvement in air purification performance.

Further, UV light emitted from the second light source module 150 has a shorter wavelength than the UV light emitted from the first light source module 140. Accordingly, the photocatalytic filter 120 is irradiated not only with the UV light emitted from the first light source module 140 but also with UV light having a shorter wavelength than the UV light emitted from the first light source module 140. As such, since the photocatalytic filter 120 is irradiated with UV light in a broader wavelength band, photocatalytic reaction on the photocatalytic filter 120 is further activated, thereby improving air purification performance of the air purifier 100.

Further, the air purifier 100 according to the illustrated exemplary embodiment achieves improvement in air purification performance not only through air purification by the photocatalytic filter 120 and the first light source module 140, but also through sterilization of dusts adhered to the HEPA filter 130.

Figure 2:
FIG. 2 and FIG. 3 are a diagram and a graph depicting a result of an experiment for testing sterilization of a HEPA filter according to exemplary embodiments.
Figure 3:
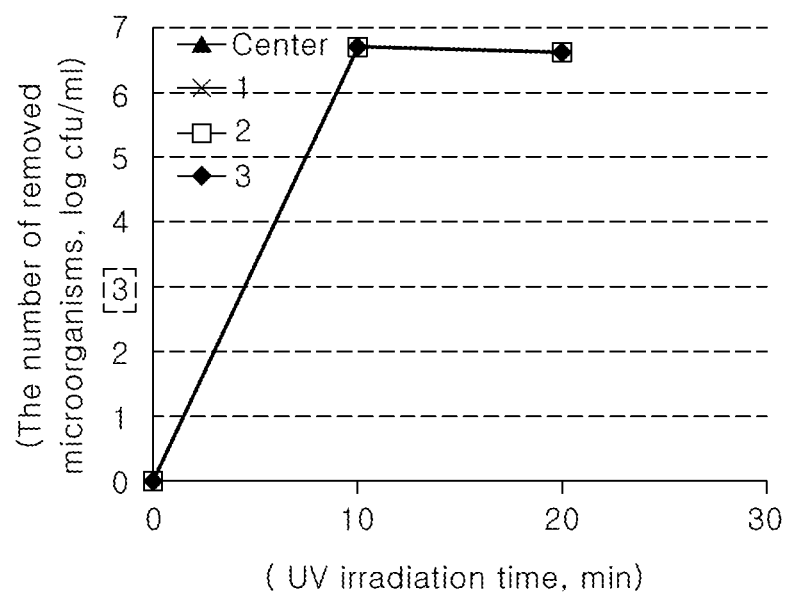

FIG. 2 and FIG. 3 are graphs depicting results of an experiment for testing sterilization of a HEPA filter according to exemplary embodiments.

The experiment was performed by irradiating the HEPA filter 130, to which microorganisms adhere in an amount of 107 CFU/ml, with UV light. In this experiment, a light source module including two light sources mounted on a substrate was used. Here, the light source module corresponds to the second light source module shown in FIG. 1. Further, an electric current of 20 mA was applied to the light sources. As the microorganisms adhered to the HEPA filter 130, *Escherichia coli* was used.

Referring to FIG. 2, the degree of sterilizing microorganisms was measured in each of four regions C, 1, 2, and 3 from the center of the HEPA filter 130 to one side thereof.

FIG. 3 is a graph depicting an experiment result. The abscissa of the graph indicates a UV irradiation time, and the ordinate of the graph indicates the number of microorganisms removed from the HEPA filter.

In the graph, the number of microorganisms removed from four regions C, 1, 2, and 3 depending upon UV irradiation time is the same. As such, it could be confirmed that the microorganisms were uniformly sterilized in the four regions. In addition, when the HEPA filter was irradiated with UV light for 10 minutes, the number of microorganisms removed from all of the four regions C, 1, 2, 3 was 7 log CFU/ml. That is, according to this experiment result, when the HEPA filter 130 was sterilized with UV light for 10 minutes, substantially all of the microorganisms adhered to the HEPA filter 130 were removed. Accordingly, when the HEPA filter 130 is sterilized with UV light, air having passed through the HEPA filter 130 may be free from microorganisms.

FIG. 4 to FIG. 11 are schematic views of air purifiers according to second to ninth exemplary embodiments.

In descriptions of the air purifiers shown in FIG. 4 to FIG. 11, repeated description of the same components as those of the air purifier 100 of FIG. 1 will be omitted.

Referring to FIG. 2 to FIG. 11, each of air purifiers 200, 300, 400, 500, 600, 700, 800, 900 according to the second to ninth exemplary embodiments includes a body 110, a photocatalytic filter 120, a HEPA filter 130, a first light source module 140, and a second light source module 150.

The air purifiers 200 to 900 according to the second to ninth embodiments are different from one another in terms of arrangement sequence of the photocatalytic filter 120, the HEPA filter 130, the first light source module 140, and the second light source module 150.

Figure 4:
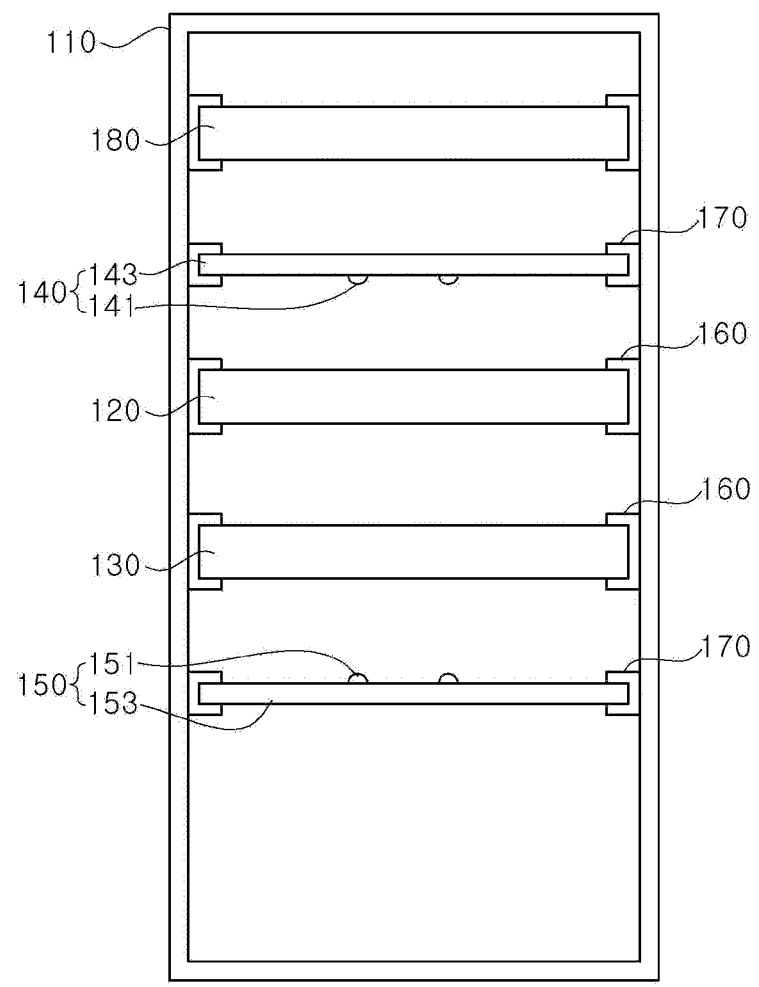
FIGS. 4, 5, 6, 7, 8, 9, 10, and 11 are schematic views of air purifiers according to second to ninth exemplary embodiments.

Referring to FIG. 4, in the air purifier 200 according to the second exemplary embodiment, the second light source module 150, the HEPA filter 130, the photocatalytic filter 120, and the first light source module 140 are sequentially arranged in the inner space of the body 110 in a direction from the suction port 111 (see FIG. 1) to the discharge port 113 (see FIG. 1).

Figure 5:
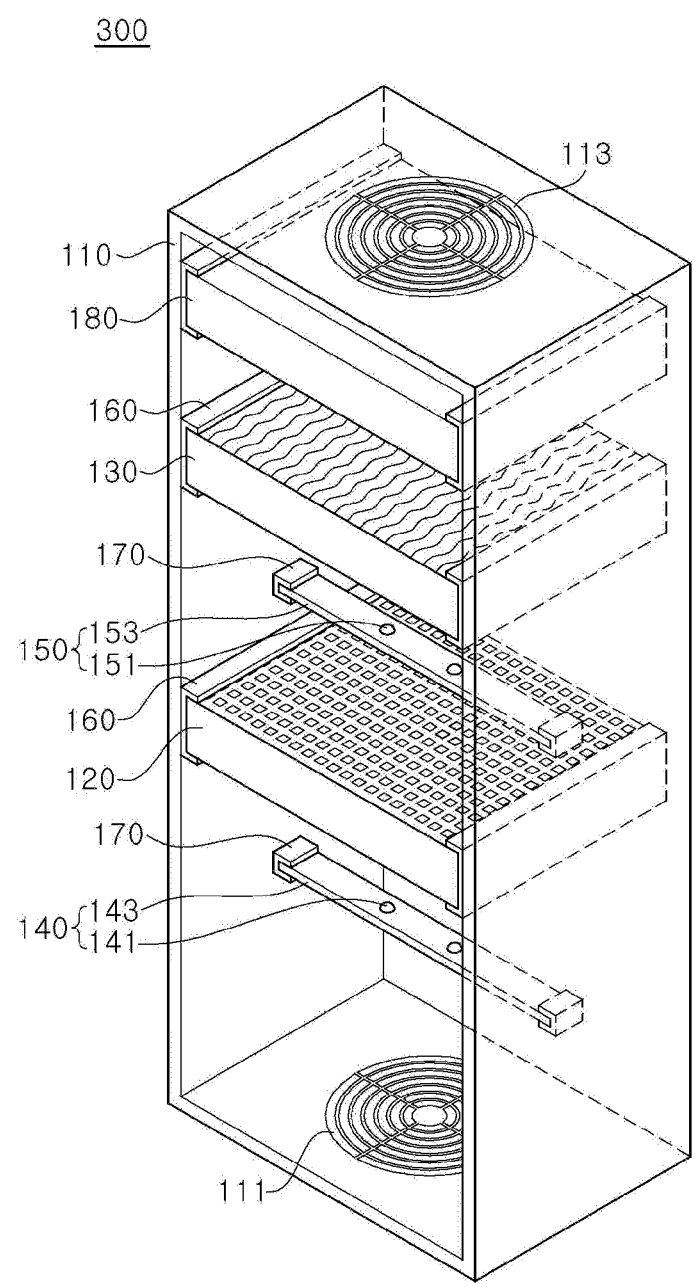

In addition, referring to FIG. 5, in the air purifier 300 according to the third exemplary embodiment, the first light source module 140, the photocatalytic filter 120, the second light source module 150, and the HEPA filter 130 are sequentially arranged in the inner space of the body 110 in the direction from the suction port 111 to the discharge port 113. With this structure, the air purifier sterilizes air in the HEPA filter 130 immediately before discharge of air. Accordingly, the cleanest air can be discharged through the air purifier 300.

Figure 6:
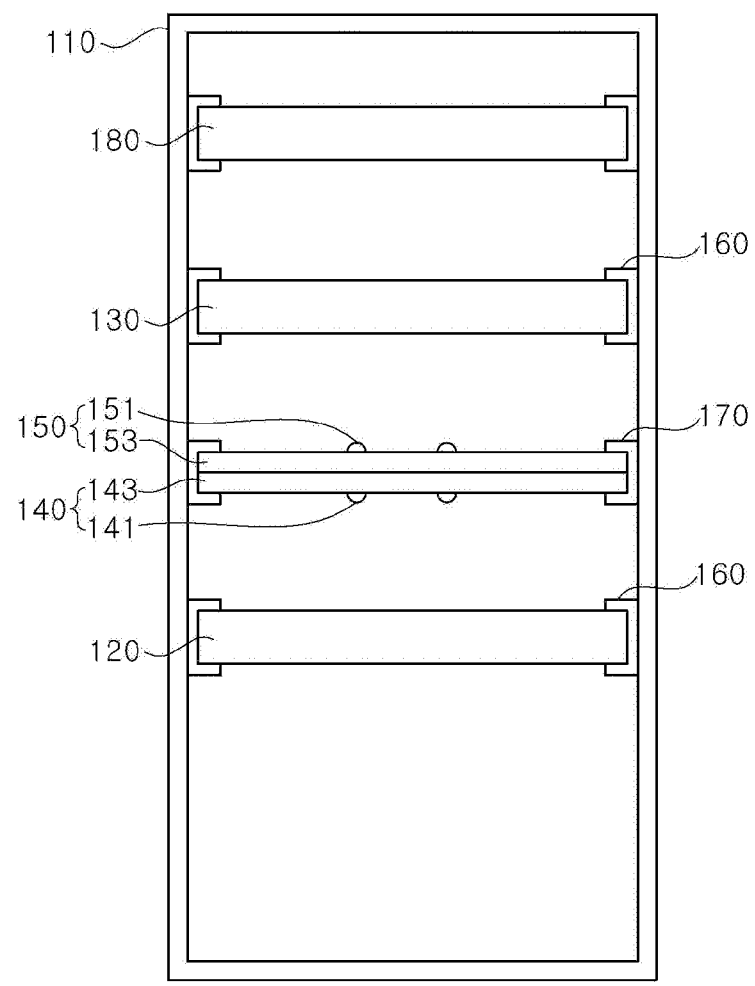
Figure 7:
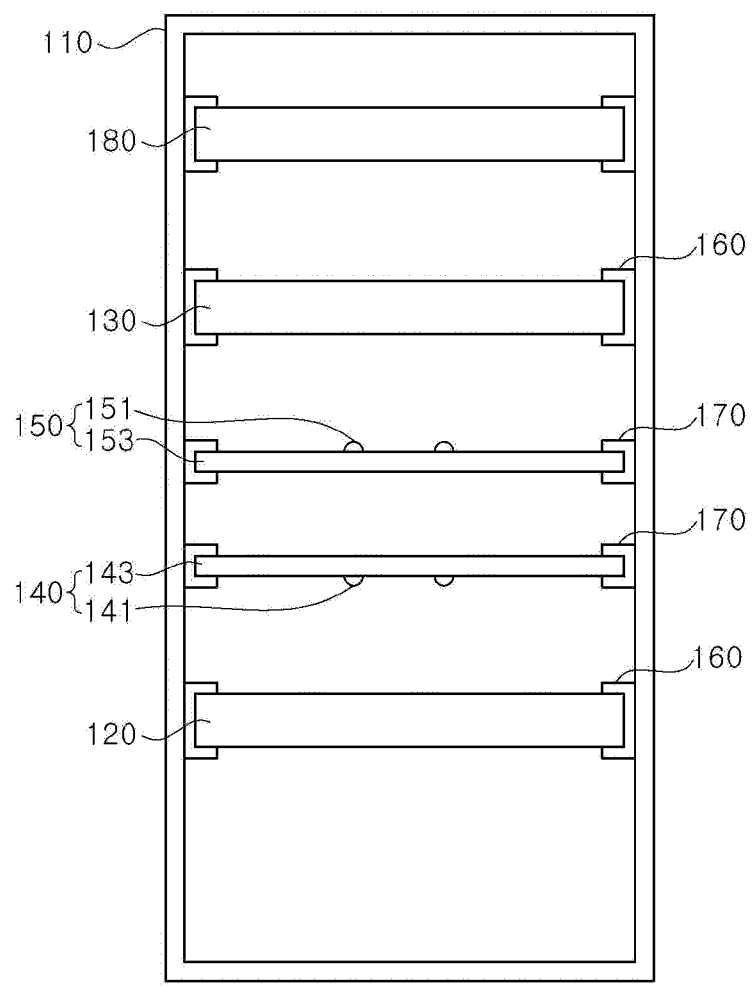
Figure 8:
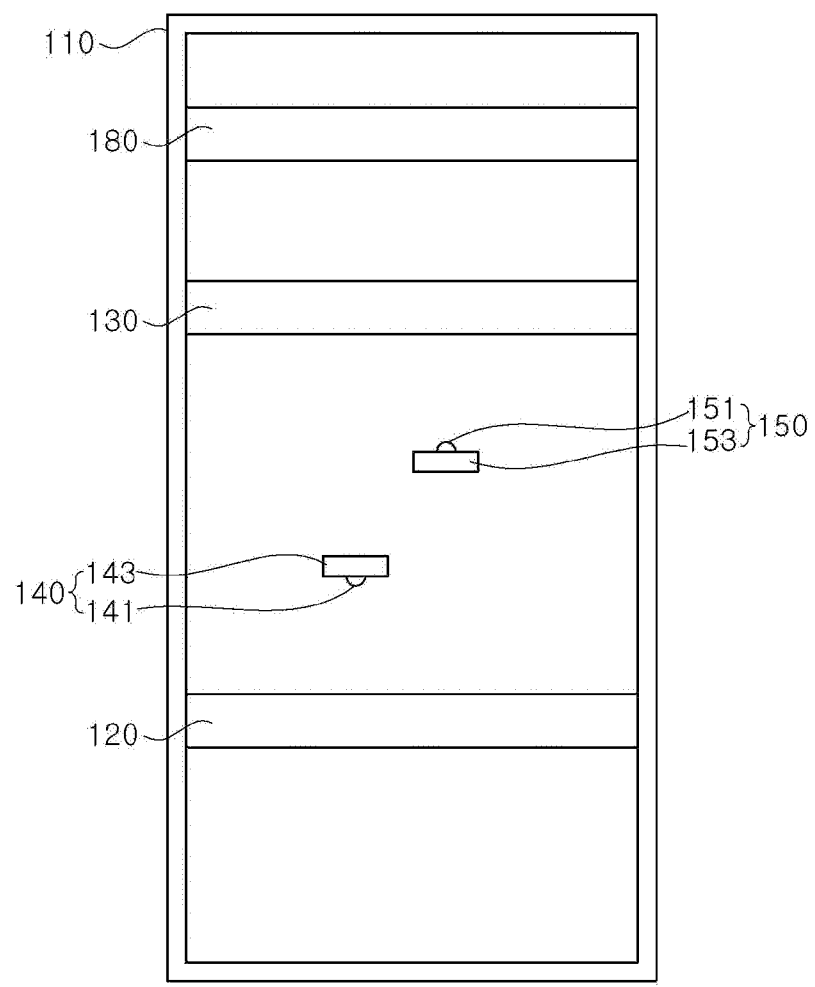

Further, referring to FIG. 6 to FIG. 10, in the air purifiers 400 to 800 according to the fourth to eighth exemplary embodiments, the photocatalytic filter 120, the first light source module 140, the second light source module 150, and the HEPA filter 130 are sequentially arranged in the inner space of the body the body 110 in the direction from the suction port 111 (see FIG. 1) to the discharge port 113 (see FIG. 1). Here, FIG. 8 is a cross-sectional view of the air purifier 600 from one side thereof.

Referring to FIG. 6, in the air purifier 400 according to the fourth exemplary embodiment, the first light source module 140 and the second light source module 150 are secured to the body 110, and the first light source module 140 contacts the second light source module 150. More particularly, a surface of the first light source module 140 opposite to another surface thereof on which the first light source 141 is mounted adjoins a surface of the second light source module 150 opposite to another surface thereof on which the second light source 151 is mounted.

Referring to FIG. 7, in the air purifier 500 according to the fifth exemplary embodiment, the first light source module 140 and the second light source module 150 are secured to the body 110, and the first light source module 140 are separated from the second light source module 150. Here, the first light source module 140 and the second light source module 150 are disposed such that one surface of the first light source module 140 faces one surface of the second light source module 150. In this manner, the first light source 141 faces the photocatalytic filter 120, and the second light source 151 faces the HEPA filter 130.

Referring to FIG. 8, in the air purifier 600 according to the sixth exemplary embodiment, the first light source module 140 is separated from the second light source module 150 so as not to overlap each other in a diagonal direction.

When the first light source module 140 is separated from the second light source module 150, as shown in FIG. 7 and FIG. 8, air can flow through a gap therebetween. Accordingly, each of the first light source module 140 and the second light source module 150 has an increased contact area with the air, thereby improving heat dissipation. Further, in the air purifier 600 shown in FIG. 8, the first light source module 140 is separated from the second light source module 150 in the diagonal direction, which may improve heat dissipation and reliability thereof than the air purifier 500 shown in FIG. 7.

Figure 9:
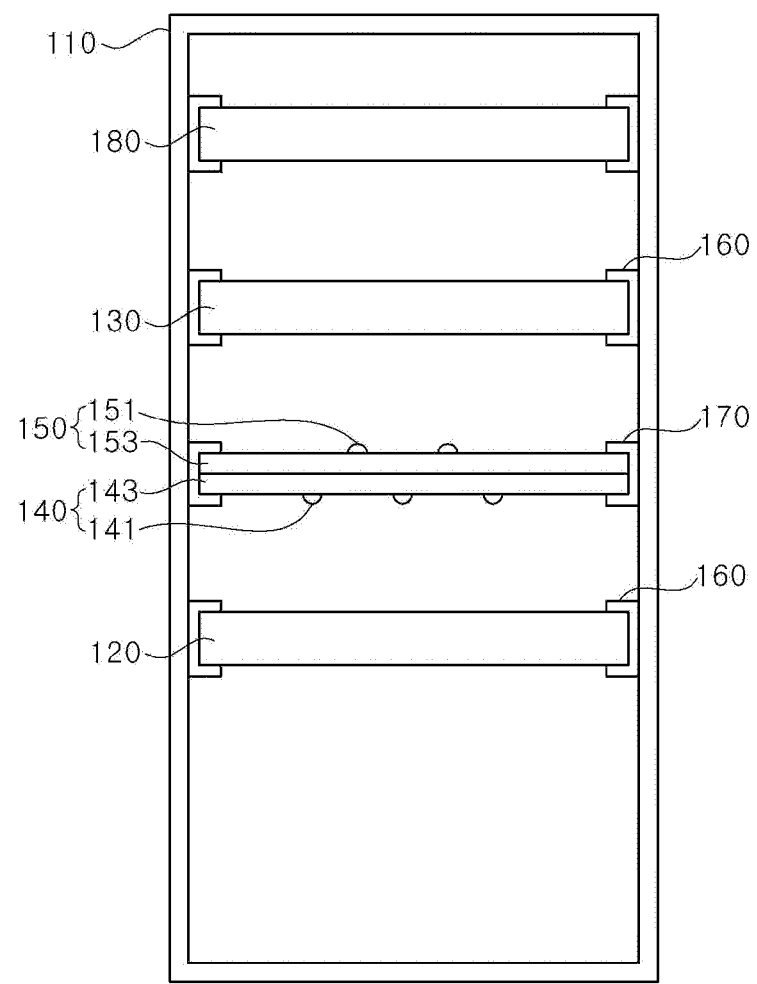
Figure 10:
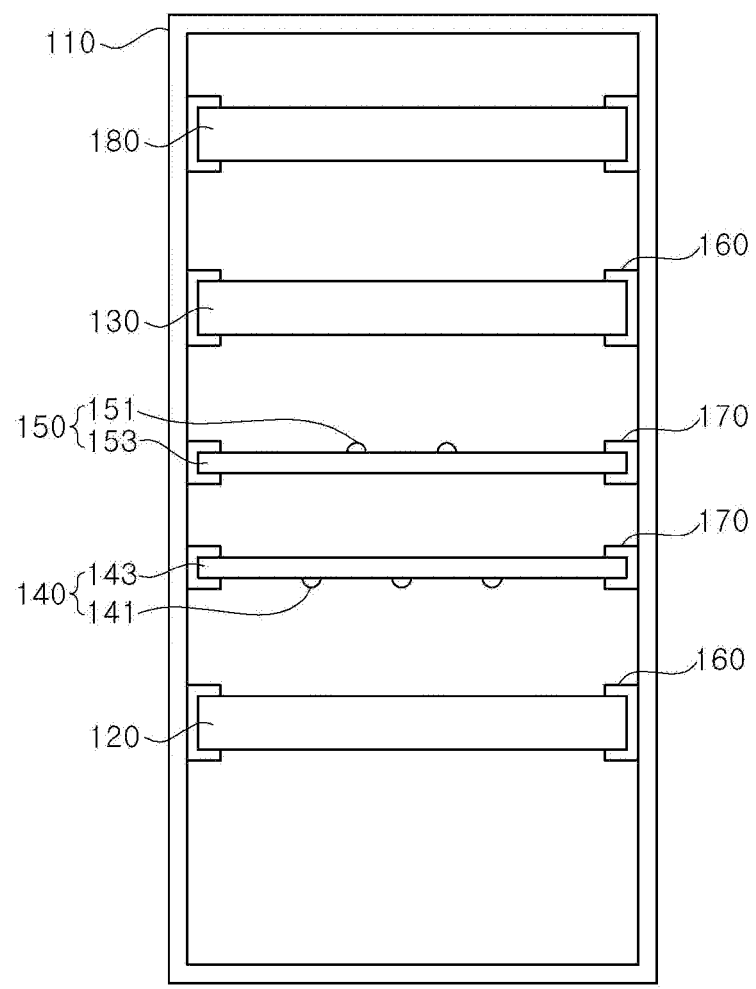

Referring to FIG. 9 and FIG. 10, in the air purifiers 700, 800 according to the seventh and eighth exemplary embodiments, the first light sources 141 and the second light sources 151 are alternately arranged. In addition, the number of first light sources 141 may be different from the number of second light sources 151. In the seventh exemplary embodiment, the first light source module 140 and the second light source module 150 contact each other. Further, in the eighth exemplary embodiment, the first light source module 140 is separated from the second light source module 150.

When the first light sources 141 are separated from the second light source 151, the air purifier can prevent heat generated from the first light sources 141 from affecting the second light source 151. Further, the air purifier can prevent heat generated from the second light source 151 from affecting the first light sources 141. Thus, with alternate arrangement of the first light sources 141 and the second light sources 151, the air purifiers 700, 800 can have improved reliability.

Figure 11:
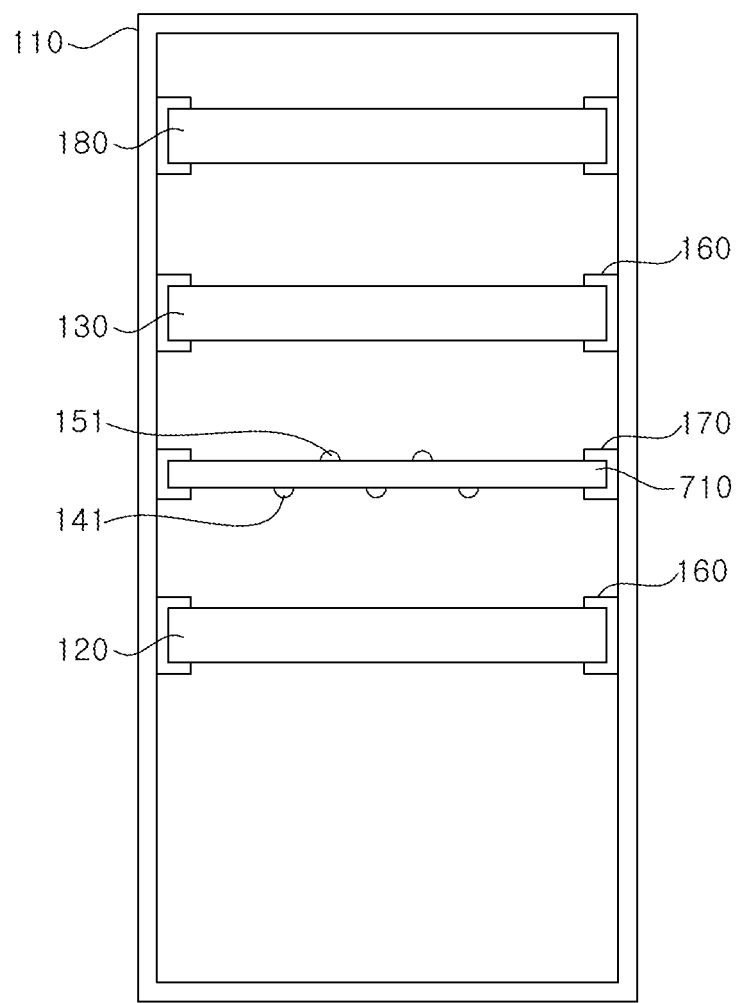

Referring to FIG. 11, in the air purifier 900 according to the ninth exemplary embodiment, the first light sources 141 and the second light sources 151 are mounted on a single light source substrate 710. In this manner, the light source module has a smaller volume than a light source module in which the first light sources 141 and the second light sources 151 are mounted on different light source substrates. Accordingly, air resistance by the light source module is reduced, thereby improving air discharge efficiency.

Figure 12:
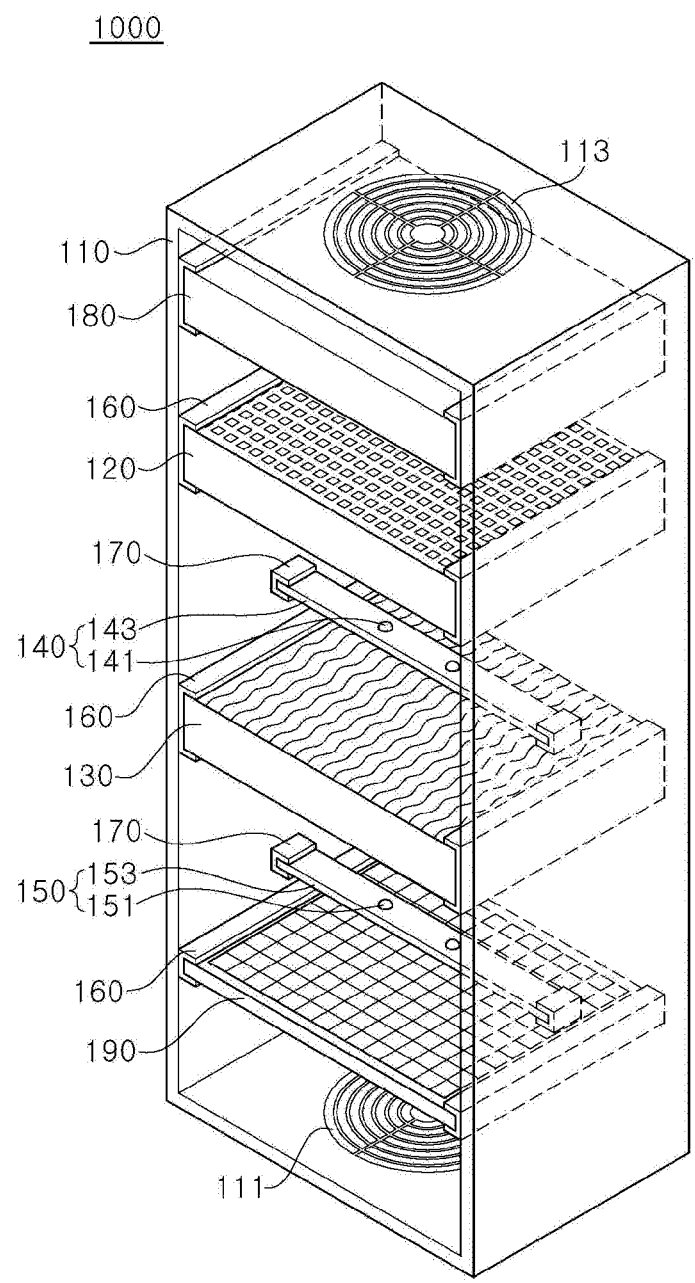
FIG. 12 is a schematic view of an air purifier according to a tenth exemplary embodiment.

FIG. 12 is a schematic view of an air purifier according to a tenth exemplary embodiment.

In description of the air purifier 1000 shown in FIG. 12, repeated description of the same components as those of the air purifier 100 of FIG. 1 will be omitted.

The air purifier 1000 according to the tenth exemplary embodiment includes a body 110, a photocatalytic filter 120, a HEPA filter 130, a first light source module 140, a second light source module 150, and a prefilter 190.

In the air purifier 1000, the prefilter 190, the second light source module 150, the HEPA filter 130, the first light source module 140, and the photocatalytic filter 120 are sequentially arranged in the direction from the suction port 111 to the discharge port 113.

The prefilter 190 may remove large dust particle from air. Accordingly, air having passed through the prefilter 190 is an air free from large dust particles. That is, the prefilter 190 prevents the large dust particle from being attached to the HEPA filter 130 and the photocatalytic filter 120, thereby preventing reduction in area where the filters react with UV light. Accordingly, efficiency in deodorization and sterilization of the HEPA filter 130 and the photocatalytic filter 120 is improved, thereby improving air purification efficiency of the air purifier 1000.

Referring to FIG. 12, the prefilter 190 is disposed adjacent to the suction port 111. Accordingly, when the dusts flow into the body through the suction port 111, large particles are removed therefrom while the dusts pass through the prefilter 190. Then, while air passes through the HEPA filter 130, fine dusts are removed therefrom. Thereafter, the air having passed through the HEPA filter 130 is purified while passing through the photocatalytic filter 120.

Although the prefilter 190 is illustrated as being disposed between the suction port 111 and the second light source module 150 in FIG. 12, the inventive concepts are not limited thereto, and the location of the prefilter 190 may be changed. For example, the prefilter 190 may be disposed at any location so long as the prefilter 190 is disposed between the suction port 111 and the HEPA filter 130.

Figure 13:
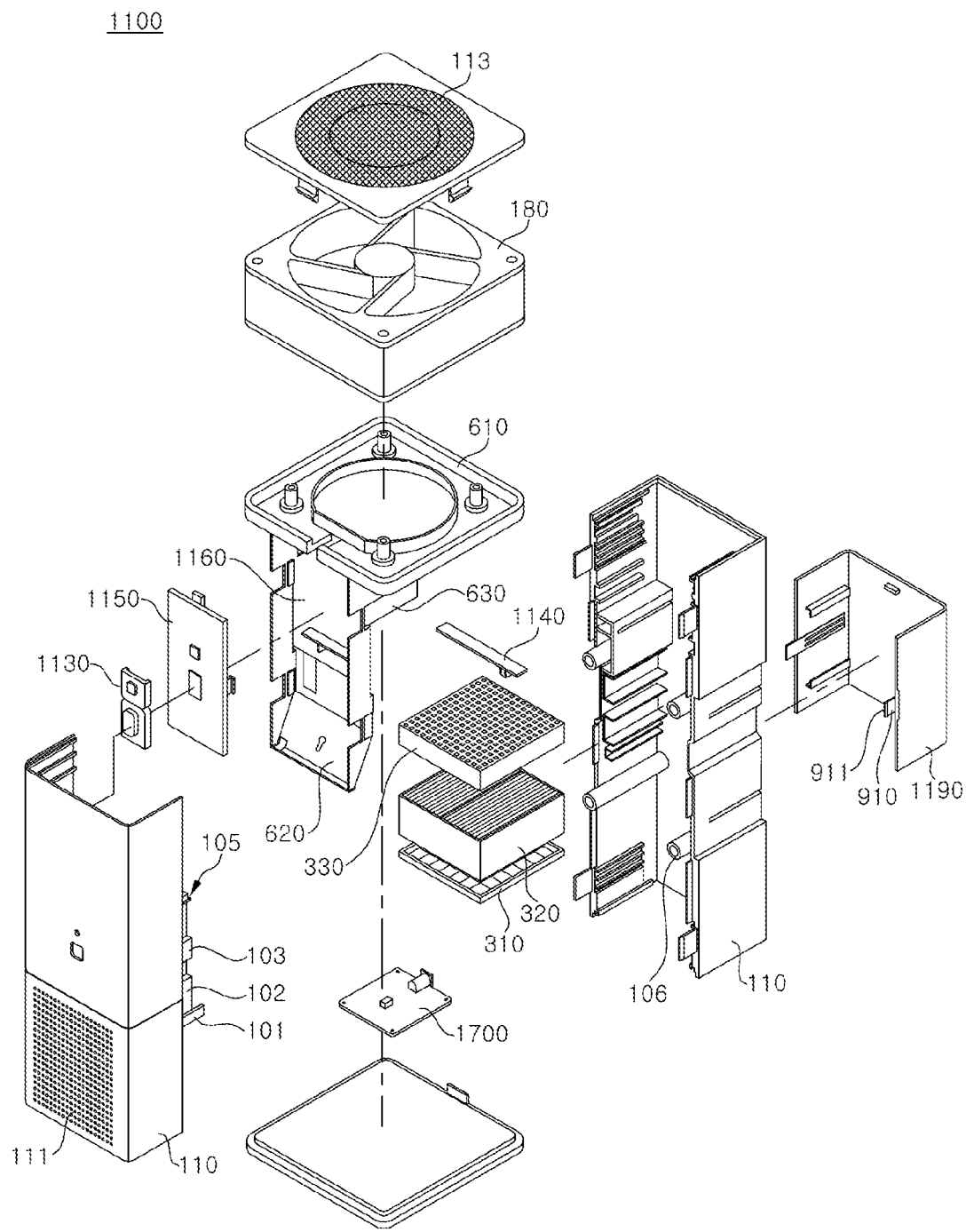
FIG. 13 is an exploded perspective view of an air purifier according to an eleventh exemplary embodiment.
Figure 14:
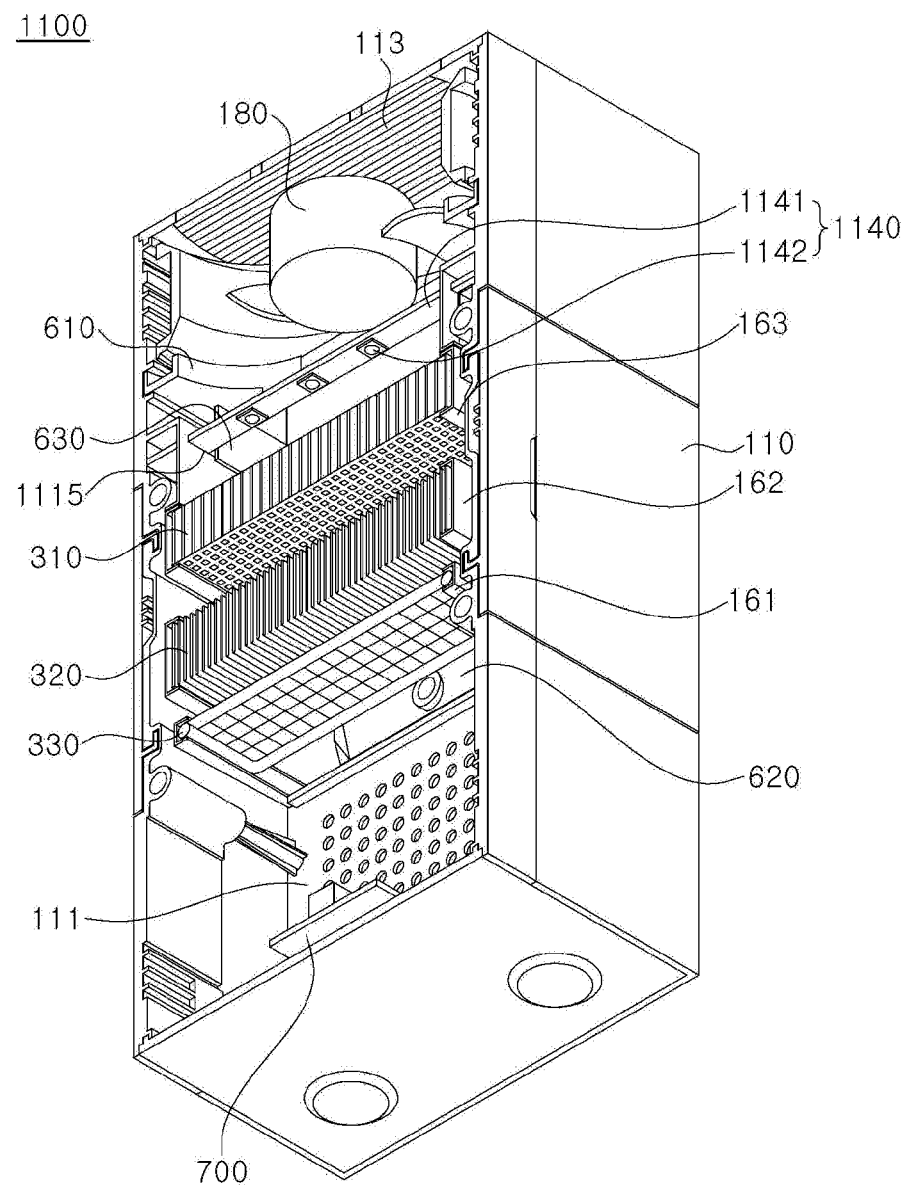
FIG. 14 is a perspective view showing the interior of the air purifier according to the eleventh exemplary embodiment.
Figure 15:
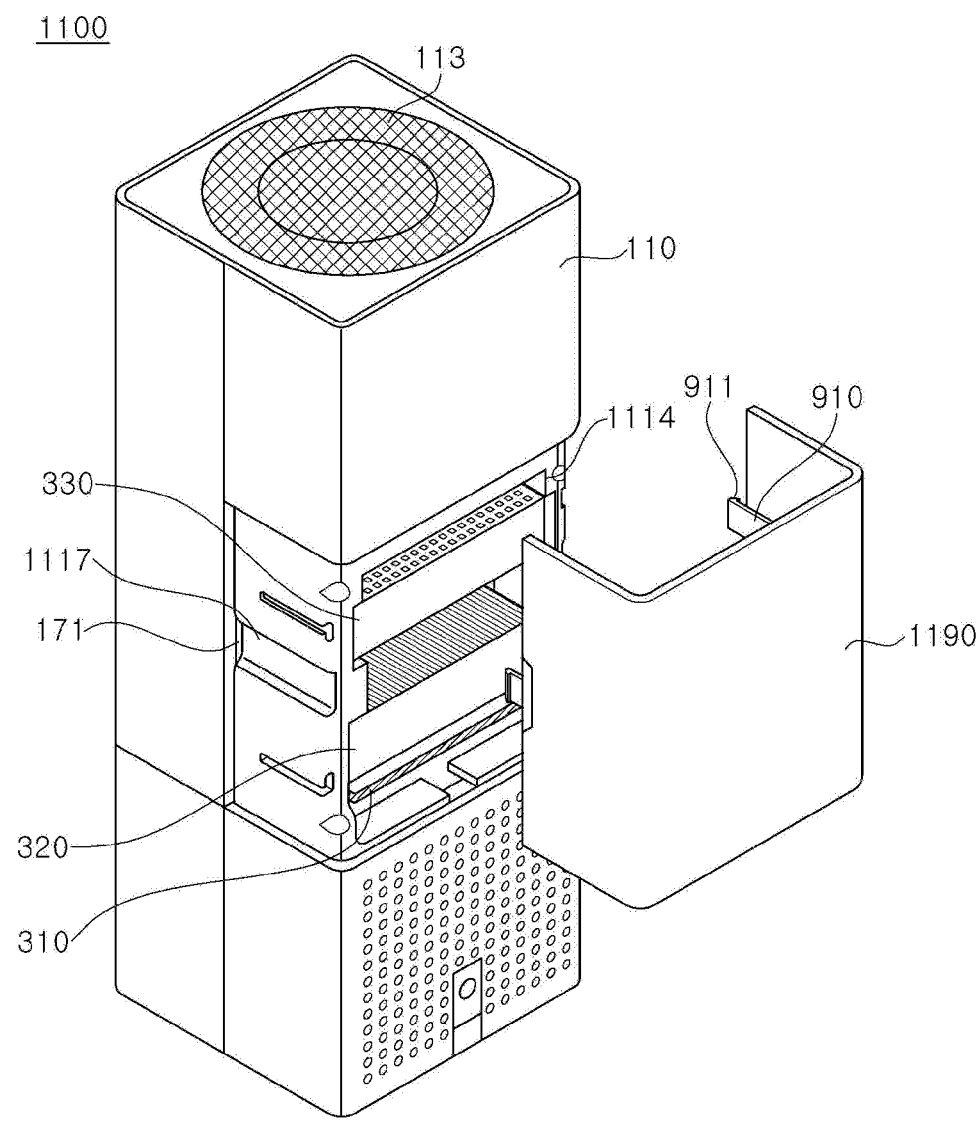
FIG. 15 is an assembly view of the air purifier according to the eleventh exemplary embodiment.

FIG. 13 to FIG. 15 are schematic views of an air purifier according to an eleventh exemplary embodiment.

FIG. 13 is an exploded perspective view of the air purifier according to the eleventh exemplary embodiment. In addition, FIG. 14 is a perspective view of the interior of the air purifier according to the eleventh exemplary embodiment. Further, FIG. 15 is an assembly view of the air purifier according to the eleventh exemplary embodiment.

Referring to FIG. 13 to FIG. 15, an air purifier 1100 includes a body 110 and a door 1190 adapted to open/close the body 110. In addition, the air purifier 1100 includes a fan 180, a first filter 310, a second filter 320, a third filter 330, a light source module 1140, a power controller 1150, and a cover 1160 inside the body 110.

The body 110 is formed with a suction port 111, a discharge port 113, a power source 1130, and a filter replacement portion 1114 on an outer wall thereof. The body 110 may be formed of metal or a resin material, such as a plastic material. Further, the body 110 may be formed in any structure including a rectangular column shape, a circular column shape, or a conical shape, so long as the body has an inner space.

Referring to FIG. 13, the body 110 is divided into a rear portion and a front portion. The rear portion of the body 110 is formed at both sides thereof with filter guide portions 105 protruding outwardly from an inner wall thereof. Each of the filter guide portions 105 includes a first filter guide 101, a second filter guide 102, and a third filter guide 103. When the front portion of the body 110 is coupled to the rear portion thereof, the first to third filter guides 101 to 103 adjoin ends of first to third filter securing portions 161 to 163 (see FIG. 14), respectively. That is, the first to third filters 310 to 330 are inserted along the first to third filter securing portions 161 to 163 and the first to third filter guides 101 to 103 may be mounted in place.

Although not shown in the drawings, a gap is at least partially formed between the inner wall of the rear portion of the body 110 and the filter guide portions 105. At least one coupling portion 106 of the front portion of the body 110 is coupled to the rear portion of the body 110 in the gap. The front portion of the body 110 may be coupled to the rear portion thereof by any method known in the art, such as screw coupling and the like.

FIG. 13 shows the body 110 divided into the front portion and the rear portion, and FIG. 14 and FIG. 15 show the body in an assembled state with the front portion thereof coupled to the rear portion thereof. That is, the body 110 is formed by coupling the front portion and the rear portion, which are separately manufactured. However, the inventive concepts are not limited to the body 110 being formed by coupling the front portion to the rear portion. For example, the body 110 may be formed by any methods known in the art so long as the body 110 has a structure capable of receiving various components therein.

The suction port 111 refers to an opening through which external air is suctioned into an inner space of the body 110. In addition, the discharge port 113 refers to an opening through which air is discharged from the interior of the body 110. That is, polluted air is suctioned into the air purifier 1100 through the suction port 111 and clean air purified inside the air purifier 1100 is discharged through the discharge port 113.

The suction port 111 and the discharge port 113 are formed on different surfaces of the body 110. For example, referring to FIG. 13 to FIG. 15, the suction port 111 is formed at a lower portion of a rear surface of the body 110 and the discharge port 113 is formed on an upper surface of the body 110. However, the inventive concepts are not limited thereto, and the locations and structures of the suction port 111 and the discharge port 113 can be variously modified so long as the suction port 111 and the discharge port 113 are formed on different surfaces of the body 110.

An air discharge area of the discharge port 113 may be the same as or different from an air suction area of the suction port 111. This structure serves to prevent air suctioned into the body 110 from remaining inside the body 110 instead of being discharged through the discharge port 113. When the air suctioned into the body 110 remains therein instead of being discharged from the body 110, an eddy current is generated inside the body 110. The eddy current obstructs the suctioned air from flowing to the discharge port 113. As such, when discharge flow of sterilized air becomes unsmooth, the air purifier 1100 can suffer from deterioration in purification efficiency, which may increase load in the fan 180 to cause noise.

Referring to FIG. 15, a periphery of the upper surface of the body 110 having the discharge port 113 formed thereon is surrounded by side surfaces of the body 110. Such a structure of the body 110 is stronger than a structure of the body having its upper surface coupled to an upper portion of the side surfaces thereof. Accordingly, the upper surface of the body 110 can be prevented from being detached from the side surface thereof from external impact, air pressure, or vibration of the fan 180. Further, it is possible to prevent noise generation from coupled portions between the surfaces of the body 110 due to vibration of the fan 180.

The power source 1130 is mounted on the inner wall of the body 110. Here, a portion of the power source 1130 is exposed outside the body 110. A portion of the power source 1130 is disposed inside the body 110 such that the power source 1130 can be electrically connected to the power controller 1150. Further, the power source 1130 and the power controller 1150 are disposed to be adjacent to each other at the same location or to contact each other. Referring to FIG. 13 to FIG. 15, the power source 1130 and the power controller 1150 are formed on the rear surface of the body 110 to be placed above the discharge port 113. However, in some exemplary embodiments, the location of the power source 1130 may be variously modified.

The power source 1130 sends a power signal to the power controller 1150 disposed inside the body 110. The power signal refers to a signal for starting or stopping power supply to the light source module 1140 and the fan 180 through the power controller 1150. The power source 1130 is connected to the power controller 1150 in a button manner or in an electrostatic manner. The button manner refers to a method of applying a power signal by applying force to the power source 1130 exposed outside the body 110 such that the power source 1130 is physically brought into contact with the power controller 1150. In addition, the electrostatic manner refers to a method of applying a power signal based on variation in electric current when the body of a user, such as a finger or the like, is brought into contact with the power source 1130 exposed outside the body 110. The power source 1130 may have any well-known structure and may be formed by any well-known method so long as the power source 1130 can apply a power signal to the power controller 1150.

The filter replacement portion 1114 refers to an opening that connects the interior of the body 110 to an exterior of the body 110. The filter replacement portion 1114 is an opening through which a filter is attached to the interior of the body 110 or is detached therefrom. Accordingly, the filter replacement portion 1114 is formed to allow the first filter 310, the second filter 320, and the third filter 330 to be exposed outside. According to the illustrated exemplary embodiment, the filter replacement portion 1114 allows very easy replacement of the first to third filters 310 to 330 therethrough. The filter replacement portion 1114 may have any structure allowing all of the first to third filters 310 to 330 to be exposed outside such that the first to third filters 310 to 330 can be detachably attached to the body therethrough.

Inside the body 110, the fan 180, the first filter 310, the second filter 320, the third filter 330, the light source module 1140, the power controller 1150, the cover 1160, and a power connector 1170 are mounted.

Referring to FIG. 13 to FIG. 15, the power controller 1150 is disposed inside the body 110. In addition, the power controller 1150 is disposed near the power source 1130 for electrical connection to the power source 1130. For example, the power controller 1150 is mounted on the inner wall of the body 110 where the power source 1130 is disposed. The power controller 1150 may be mounted on the inner wall of the body 110 by screw coupling or a bonding agent. The power controller 1150 supplies electric power to the light source module 1140 and the fan 180 in response to a power signal from the power source 1130. Here, the light source module 1140 emits light and the fan 180 is operated, while power is supplied thereto through the power controller 1150. The power controller 1150 allows continuous power supply to the light source module 1140. Further, the power controller 1150 may supply electric power to the light source module 1140 in a pulse driving manner. When the power controller 1150 supplies electric power to the light source module 1140 in the pulse driving manner, light sources 1142 are repeatedly turned on/off. Accordingly, the air purifier 1100 can reduce power consumption, as compared with the structure to which electric power is continuously supplied.

In addition, the power controller 1150 may stop power supply to the light source module 1140 and the fan 180 in response to a power signal from the power source 1130 when the light source module 1140 and the fan 180 are supplied with power. In this manner, the power controller 1150 may repeatedly start and stop the power supply in response to a power signal from the power source 1130.

The power controller 1150 is electrically connected to the light source module 1140 and the fan 180 through a cable. Further, the power controller 1150 may be electrically connected to an exterior power supply or an interior power supply through a cable.

In the illustrated exemplary embodiment, the power controller 1150 is illustrated as supplying electric power to the light source module 1140 and the fan 180. However, components receiving electric power supplied from the power controller 1150 are not limited thereto. Alternatively, the power controller 1150 may supply electric power only to the light source module 1140. Alternatively, the power controller 1150 may be electrically connected not only to the light source module 1140 but also to any components requiring power supply. In addition, the power controller 1150 may supply electric power to other components including the light source module 1140 in the pulse driving manner. Alternatively, the power controller 1150 may supply electric power to the light source module 1140 only in the pulse driving manner while supplying electrical power to other components in a continuous manner.

The cover 1160 is mounted on the inner wall of the body 110 and is formed to cover the power controller 1150. The cover 1160 can protect the power controller 1150 from external impact and can prevent damage thereto due to physical contact with other components.

The cover 1160 may be formed at one side thereof with a fan securing portion 610. The fan securing portion 610 is formed such that a surface of the fan securing portion 610 securing the fan 180 is parallel to the discharge port 113. Accordingly, the fan 180 mounted on the fan securing portion 610 can be secured inside the body 110, with the fan 180 disposed in parallel to the discharge port 113. The fan 180 may be coupled to the fan securing portion 610 by any coupling methods known in the art, such as a bonding agent or screws.

When the fan 180 is secured by the fan securing portion 610, a side surface of the fan 180 may be separated from the inner wall of the body 110. With this structure, the air purifier 1100 can prevent noise from the fan 180 or other components from leaking outside the air purifier 1100 through a space between the fan 180 and the body 110.

The cover 1160 is formed at the other side thereof with an air flow guide facet 620 having an inclination. The air flow guide facet 620 is tilted between the suction port 111 and the first filter 310. Referring to FIG. 13 to FIG. 15, the air flow guide facet 620 is tilted to have a gradually increasing height from the suction port 111 toward the first filter 310. Accordingly, air suctioned into the body 110 through the suction port 111 flows along the air flow guide facet 620 and then passes through the first filter 310. The air flow guide facet 620 can prevent generation of an eddy current or loss of the suctioned air through the suction port 111 due to collision with the inner wall of the body 110 or other components of the air purifier 1100.

The cover 1160 may include a light source module support 630. The light source module support 630 is disposed between the fan securing portion 610 and the third filter 330. The light source module support 630 supports both sides of the light source module 1140 in one direction. For example, the light source module support 630 allows the light source module 1140 to be placed at the center of the third filter 330.

The cover 1160 may be formed with cable passages. The cable passages refer to paths through which cables connecting the components of the air purifier 1100 pass. The locations and the number of cable passages may be varied depending upon arrangement of the components.

The fan 180 is mounted on the fan securing portion 610 and is disposed to be parallel to the discharge port 113. Here, a rotational axis of the fan 180 is perpendicular to the discharge port 113. For example, the fan 180 is an axial flow fan.

The fan 180 allows sterilized air to be discharged from the air purifier 1100 by suctioning the sterilized air from the body 110 and forcing the suctioned air to be discharged through the discharge port 113.

The light source module 1140 includes a light source substrate 1141 and light sources 1142. The light source substrate 1141 is formed with a circuit configured to receive electric power through the power controller 1150 and to operate the light sources 1142. The light sources 1142 are disposed on one surface of the light source substrate 1141 and are electrically connected to the light source substrate 1141. Further, the light source 1142 emits UV light in a sterilization wavelength range and is a spot light source.

The light source module 1140 is disposed between the fan 180 and the third filter 330. One surface of the light source module 1140 having the light sources 1142 mounted thereon faces the third filter 330 and the other surface thereof faces the fan 180. Accordingly, light emitted from the light sources 1142 can be directed toward the third filter 330 and the light source substrate 1141 can prevent light from being discharged through the fan 180 or the discharge port 113 to the outside. In addition, the light source module 1140 is disposed adjacent to the fan 180 to dissipate heat from the light source module 1140, whereby the air purifier 1100 can have improved heat dissipation efficiency.

The body 110 may have light source module grooves 1115 formed on the inner wall thereof. The light source module grooves 1115 receive both sides of the light source module 1140. Referring to FIG. 14, the light source module grooves 1115 are elongated in one direction. Here, the one direction refers to a direction in which the light source module support 630 is formed.

Accordingly, the light source module 1140 is inserted into the light source module grooves 1115 and mounted inside the body 110 while being supported by the light source module support 630. That is, the light source module 1140 is secured inside the body 110 by being fitted between the inner wall of the body 110 and the light source module support 630.

In the illustrated exemplary embodiment, the light source module 1140 is mounted inside the body 110 by the light source module support 630. However, the structure for mounting the light source module 1140 is not limited thereto. For example, in some exemplary embodiments, the light source module support 630 may be omitted so long as the light source module grooves 1115 are formed to correspond to both sides of the light source module 1140. Alternatively, the light source module grooves 1115 may be formed in any structure enabling support of the light source module 1140 in an opposite direction to the light source module support 630. In this manner, the structures of the light source module grooves 1115 and the light source module support 630 may be variously modified, as needed.

In some exemplary embodiments, the light source module 1140 may be disposed so as not to be exposed from the filter replacement portion 1114. That is, the light source module 1140 may be disposed at a location further indented from one side of the filter replacement portion 1114 toward the fan 180. With this arrangement, the air purifier 1100 can prevent the light from being discharged to the outside when light is emitted from the light source module 1140, with the door 1190 open. However, the inventive concepts are not limited to the light source module 1140 from not being exposed through the filter replacement portion 1114.

The first to third filters 310 to 330 are disposed between the light source module 1140 and the suction port 111. Each of the first to third filters 310 to 330 is formed with a plurality of through holes. The through holes of the first filter 310 have a larger diameter than those of the second filter 320. For example, the first filter 310 is a prefilter and the second filter 320 is a HEPA filter. In addition, the third filter 330 is a photocatalytic filter performing photocatalytic reaction with light emitted from the light source module 1140. The through holes of the third filter 330 provided as the photocatalytic filter have a rectangular cross-section. The photocatalytic filter including the through holes each having a rectangular cross-section can be more easily manufactured than a typical photocatalytic filter including through holes each having a honeycomb-shaped cross-section.

Referring to FIG. 13 to FIG. 15, the first to third filters 310 to 330 are disposed to block an air passage between the cover 1160 and the inner wall of the body 110. That is, one of side surfaces of the first to third filters 310 to 330 closely contacts the cover 1160 and the other side surfaces thereof closely contact the inner wall of the body 110. Accordingly, air suctioned through the suction port 111 is required to pass through the through holes of the first to third filters 310 to 330 in order to escape through the discharge port 113.

The first to third filters 310 to 330 are disposed in the sequence of the first filter 310, the second filter 320, and the third filter 330 with reference to the suction port 111.

The first filter 310 acting as the prefilter serves to filter large dust particles moving together with air.

The second filter 320 acting as the HEPA filter serves to filter fine dusts having passed through the first filter 310. The second filter 320 prevents the fine dusts from contacting the third filter 330 or from being accumulated thereon. When the fine dusts are accumulated on the third filter 330, a contact area between light emitted from the light sources 1142 and the third filter 330 is reduced. As such, the second filter 320 can prevent deterioration in sterilization of air by the third filter 330 by filtering the fine dusts.

The third filter 330 acting as the photocatalytic filter serves to sterilize air passing therethrough from reaction with light emitted from the light sources 1142. In this manner, the air purifier 1100 can perform removal of large dust particles and fine dusts and sterilization of air at the same time using the first to third filters 310 to 330.

According to the exemplary embodiments, a distance between the third filter 330 and the light source 1142 is greater than or equal to a value represented by Equation: the area of the third filter/[2× tan(angle of light beam/2)×0.2] and smaller than or equal to a value represented by Equation: the area of the third filter/[2× tan(angle of light beam/2)×2]. Here, the area of the third filter refers to an area of a surface of the third filter 330 facing the light source 1142.

If the distance between the third filter 330 and the light source 1142 is smaller than the value represented by Equation: the area of the third filter/[2× tan(angle of light beam/2)×0.2], the distance between the third filter 330 and the light source 1142 is too narrow, thereby making it difficult to uniformly irradiate the entirety of the third filter 330. Accordingly, in order to allow the entirety of the third filter 330 to be uniformly irradiated with light, the air purifier 1100 requires a plurality of light sources, which increases manufacturing costs.

If the distance between the third filter 330 and the light source 1142 is greater than the value represented by Equation: the area of the third filter/[2× tan(angle of light beam/2)×2], the distance between the third filter 330 and the light source 1142 increases, thereby causing reduction in light intensity. As a result, efficiency in photocatalytic reaction is reduced.

The air purifier 1100 according to the illustrated exemplary embodiment maintains a suitable distance between the light sources 1142 and the third filter 330, thereby enabling efficient air purification.

In some exemplary embodiments, the air purifier 1100 may be provided with a carbon filter to remove odor. That is, the filters provided to the air purifier 1100 are not limited to the aforementioned filters. The air purifier 1100 may be modified into any structure so long as the air purifier 1100 includes the photocatalytic filter and at least one of the HEPA filter, the prefilter, and the carbon filter therein.

The body 110 is formed on the inner wall thereof with a first filter securing portion 161, a second filter securing portion 162, and a third filter securing portion 163. The first to third filters 310 to 330 are secured inside the body 110 by inserting side surfaces of the first to third filters 310 to 330 into the first filter securing portion 161 to the third filter securing portion 163, respectively.

The body 110 may further include a power connector 1170 disposed therein. The power connector 1170 allows electric power from an exterior power supply to be supplied to the power controller 1150.

In addition, both the inner wall of the body 110 and the cover 1160 have a black color.

The door 1190 is formed to cover the filter replacement portion 1114 of the body 110. The filter replacement portion 1114 of the body 110 is opened and closed according to opening/closing movement of the door 1190. FIG. 13 to FIG. 15 shows that the door 1190 is opened when the door 1190 is completely separated from the body 110. When the door 1190 is opened, the first filter 310, the second filter 320, and the third filter 330 are exposed to the outside through the filter replacement portion 1114. The door 1190 completely separated from the body 110 is closed by coupling the door 1190 to the body 110 in a sliding manner. The door 1190 is detachably attached to the body 110 while moving from the front side of the body 110 toward the rear side thereof. The door 1190 is formed with door guides 910 for opening and closing the body 110. The door guides 910 are formed at both sides of the door 1190 to continuously protrude from an inner wall of the door 1190. Further, the body 110 is formed with door guide grooves 1117 on an outer wall thereof at both sides thereof. The door guide grooves 1117 are formed where the door guides 910 are brought into contact with the door guide grooves 1117, and have a groove structure to receive the door guides 910 inserted into the door guide grooves 1117. According, the door 1190 is coupled to the body 110 by inserting the door guides 910 into the door guide grooves 1117. Here, each of the door guides 910 may be formed with a door securing portion 911 having a protruding structure. Further, each of the door guide grooves 1117 may be formed with a door securing groove 171 corresponding to the door securing portion 911. When the door 1190 is brought into complete contact with the body 110, the door securing portions 911 are inserted into the door securing grooves 171 so that the door 1190 can be secured to the body 110. The door securing portion 911 and the door securing groove 171 will be described in more detail below where the door 1190 is coupled to the body 110.

Conventionally, the body of the air purifier is required to be completely disassembled for replacement of filters. Otherwise, it is necessary to replace the entire air purifier. However, the air purifier 1100 according to the illustrated exemplary embodiment allows replacement of filters only through separation of the door 1190. Accordingly, it is possible to reduce time and cost for replacement of the filters.

The following drawings are briefly shown for convenience of description and understanding. For structures of components omitted in the following drawings may be found above with reference to FIG. 13 to FIG. 15.

Figure 16:
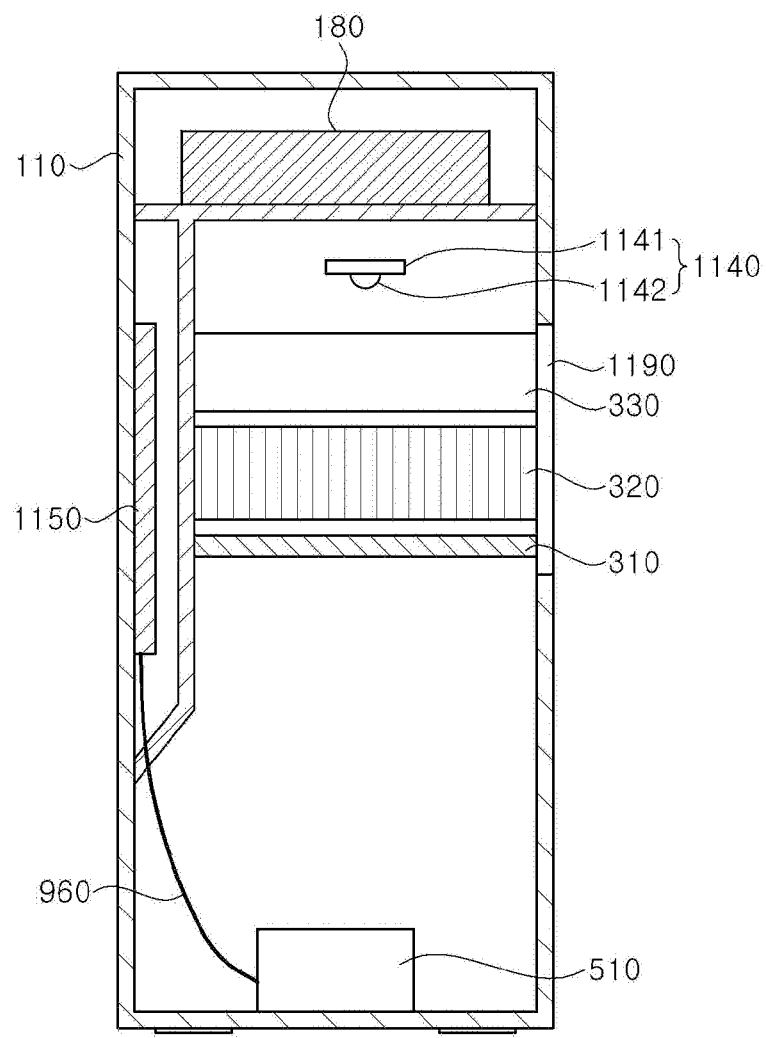
FIG. 16 is a schematic view of an air purifier according to a twelfth exemplary embodiment.

FIG. 16 is a schematic view of an air purifier according to a twelfth exemplary embodiment.

In descriptions of an air purifier 1200 according to the twelfth exemplary embodiment, repeated description of the same components as those of the air purifier 1100 of FIG. 15 will be omitted to avoid redundancy.

Referring to FIG. 16, the air purifier 1200 includes a power storage 510 received therein. The power storage 510 is disposed inside the body 110 and is electrically connected to the power controller 1150. The power controller 1150 supplies electric power stored in the power storage 510 to the fan 180 and the light source module 1140 in response to a power signal from the power source 1130 (see FIG. 13).

According to the illustrated exemplary embodiment, when electric power stored in the power storage 510 in the air purifier 1200 is completely consumed, the power storage 510 may be replaced by another power storage 510. Alternatively when electric power stored in the power storage 510 is completely consumed, the power storage 510 may be connected to an external power supply to be charged with power. For example, the power storage 510 may be a consumable battery or a rechargeable battery.

When the air purifier 1200 receives the power storage 510 therein, the air purifier 1200 does not require continuous connection to an external power supply. Accordingly, since the air purifier 1200 is not required to be continuously connected to the external power supply through a cable 960, the air purifier 1200 reduces spatial restriction for installation of the air purifier 1200.

Figure 17:
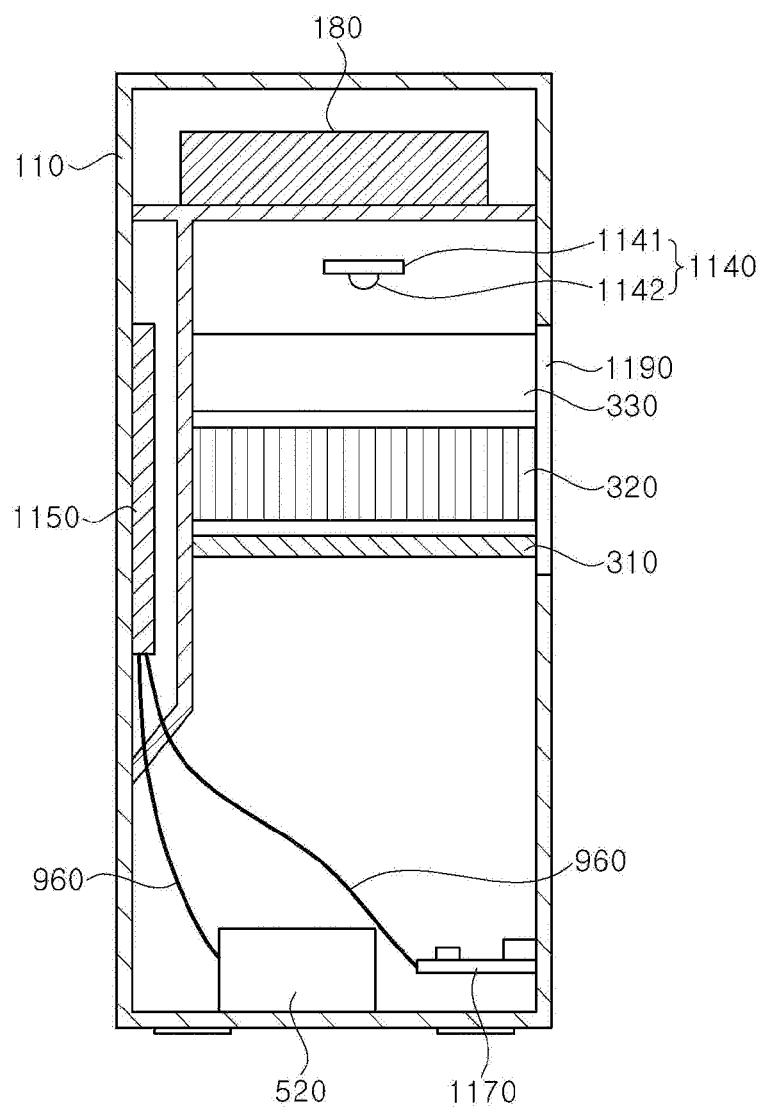
FIG. 17 and FIG. 18 are schematic views of air purifiers according to thirteenth and fourteenth exemplary embodiments.
Figure 18:
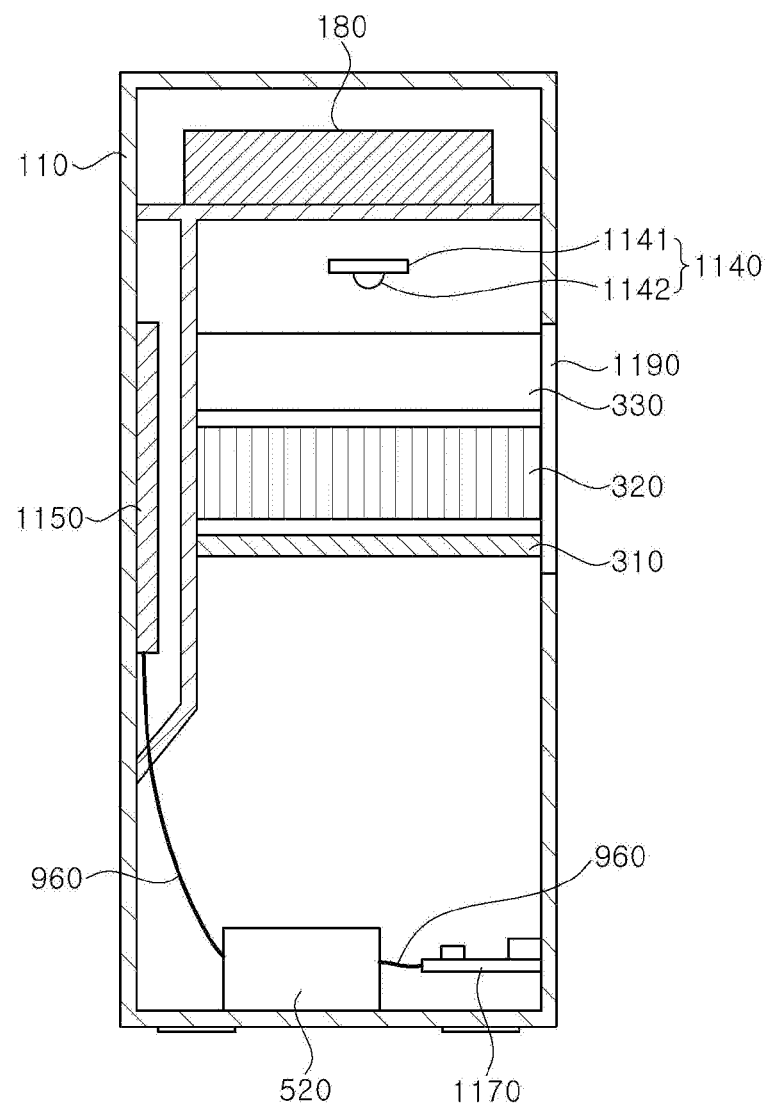

FIG. 17 and FIG. 18 are schematic views of air purifiers according to thirteenth and fourteenth exemplary embodiments.

In descriptions of air purifiers 3000, 4000 according to the thirteenth and fourteenth exemplary embodiments, repeated description of the same components as those of the air purifier 1100 of FIG. 15 will be omitted.

Referring to FIG. 17 and FIG. 18, each of the air purifiers 3000, 4000 according to the thirteenth and fourteenth exemplary embodiments includes a preliminary power storage 520 inside the body. Referring to the drawings, the power controller 1150 is connected to the preliminary power storage 520 and an external power supply.

In the air purifier 1300 according to the thirteenth exemplary embodiment, the power controller 1150 receives electric power supplied from the external power supply. However, when the power controller 1150 cannot receive electric power from the power supply due to failure of the cable 960 or the like, the power controller 1150 may receive electric power supplied from the preliminary power storage 520. The preliminary power storage 520 may be selected from any devices capable of preliminarily storing electric power. For example, the preliminary power storage 520 may be a rechargeable battery. The power controller 1150 is connected to the preliminary power storage 520 and a power connector 1170 connected to the external power source through the cables 960.

In FIG. 17, the power controller 1150 is illustrated as being connected to the preliminary power storage 520 and the power connector 1170 connected to the external power source via the separate cables 960. However, in the air purifier 1400 according to the fourteenth exemplary embodiment shown in FIG. 18, the power controller 1150 may be connected to the preliminary power storage 520, which is connected to the external power supply. In the illustrated exemplary embodiment, the power controller 1150 is connected to the preliminary power storage 520 through a cable 960 and is also connected to the external power supply through another cable 960. In this structure, the preliminary power storage 520 may supply some of electric power supplied from the external power supply to the power controller 1150 and may store (charge) the remaining electric power as preliminary electric power.

Figure 19:
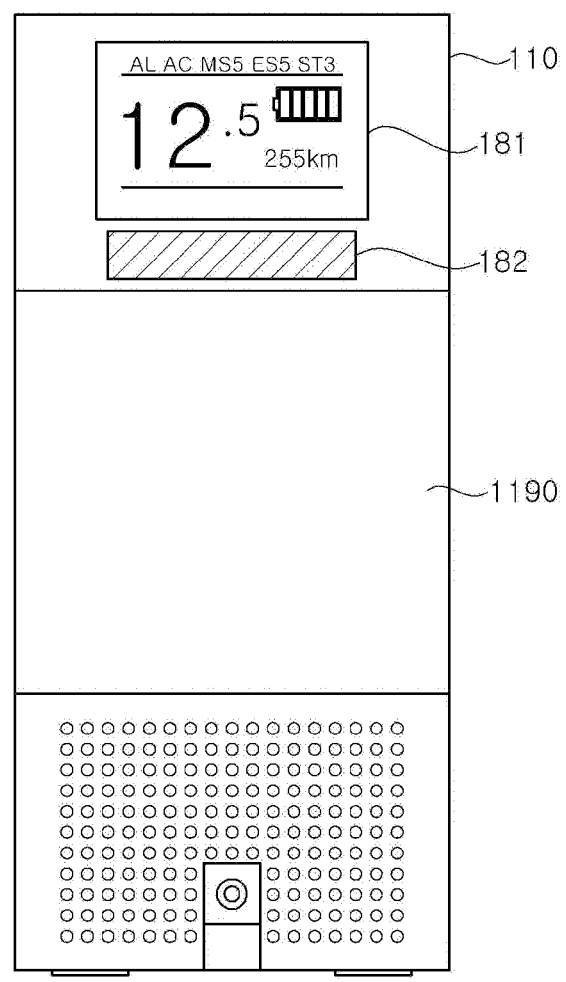
FIG. 19 is a schematic view of an air purifier according to a fifteenth exemplary embodiment.

FIG. 19 is a schematic view of an air purifier according to a fifteenth exemplary embodiment.

In descriptions of an air purifier 1500 according to the fifteenth exemplary embodiment, repeated descriptions of the same components as those of the air purifiers according to the eleventh to fourteenth exemplary embodiments will be omitted.

Referring to FIG. 19, the air purifier 1500 includes an input unit 182 and an output unit 181.

The input unit 182 and the output unit 181 are formed on the outer wall of the body 110. The output unit 181 visually represents information about the air purifier 1500 and information input through the input unit 182. For example, the output unit 181 may be a liquid crystal display (LED) and the input unit 182 may be a touch pad. However the types of the output unit 181 and the input unit 182 are not limited thereto, and any display device and input device applicable to an air purifier may be used.

When information such as a filter replacement date is input through the input unit 182, the information input to the output unit 181 is displayed thereon. A user can determine a filter replacement time based on the information displayed on the output unit 181. In addition, a message may be input through the input unit 182 and a message input to the output unit 181 may be displayed thereon. With such a function, another user can check the message of the user. In addition, the output unit 181 may display information, such as date, time, and the like.

In the illustrated exemplary embodiment, the input unit 182 and the output unit 181 are illustrated as separate components. However, the input unit and the output unit 181 may be formed as a single component capable of performing both input and output, such as a touchscreen.

Figure 20:
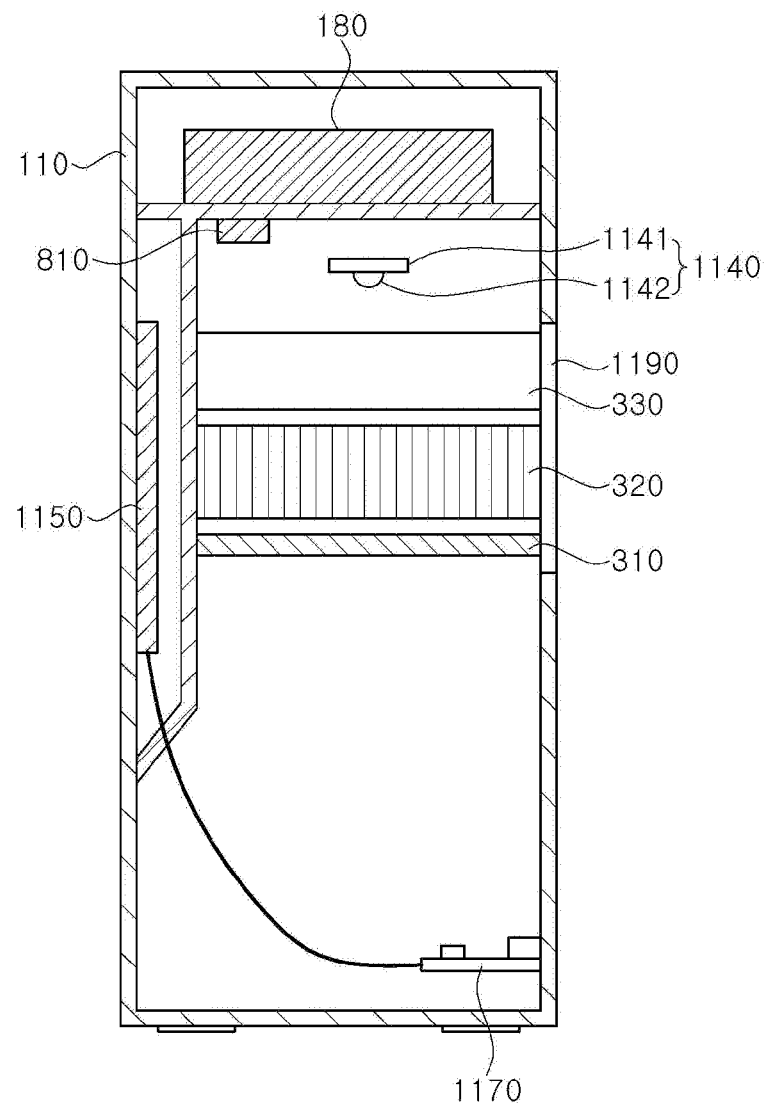
FIG. 20 is a schematic view of an air purifier according to a sixteenth exemplary embodiment.

FIG. 20 is a schematic view of an air purifier according to a sixteenth exemplary embodiment.

In descriptions of an air purifier 1600 according to the sixteenth exemplary embodiment, repeated description of the same components as those of the air purifiers according to the eleventh to fifteenth exemplary embodiments will be omitted.

Referring to FIG. 20, the air purifier 1600 according to the sixteenth exemplary embodiment includes a photo sensor 810.

The photo sensor 810 detects the intensity of light reflected from the first to third filters 310 to 330. As the amount of dust attached to the first to third filters 310 to 330 increases, the intensity of light reflected from the first to third filters 310 to 330 decreases.

The photo sensor 810 may compare the intensity of detected light with a predetermined reference value. As a result of comparison, if the intensity of the light is smaller than the predetermined reference value, the photo sensor 810 transmits a filter replacement signal to the output unit 181 (see FIG. 19). In response to the filter replacement signal from the photo sensor 810, the output unit 181 (see FIG. 19) outputs a filter replacement alarm to inform a user of a filter replacement time.

The output unit 181 may have the same configuration as the output unit 181 (see FIG. 19) according to the fifteenth exemplary embodiment. The output unit 181 may be a speaker configured to output sound or a light emitting device configured to emit light having a color. Further, the output unit 181 may include at least two of devices outputting text, light, and sound. Thus, the output unit 181 may output a filter replacement alarm including at least one of text, light, and sound to the outside.

In FIG. 20, the photo sensor 810 is disposed to detect the intensity of light reflected from the third filter 330. Alternatively, the air purifier 1600 may include a plurality of photo sensors 810 to detect the intensity of light reflected from each of the first to third filters 310 to 330. In this structure, each of the plural photo sensors 810 generates and sends a filter replacement signal to the output unit 181 (see FIG. 19). The output unit 181 (see FIG. 19) may output a filter replacement alarm with respect to each of the first to third filters 310 to 330 in response to the filter replacement signal from the photo sensor 810. Accordingly, the air purifier 1600 according to the illustrated exemplary embodiment enables replacement of a filter requiring replacement instead of replacing all of the first to third filters 310 to 330.

Figure 21:
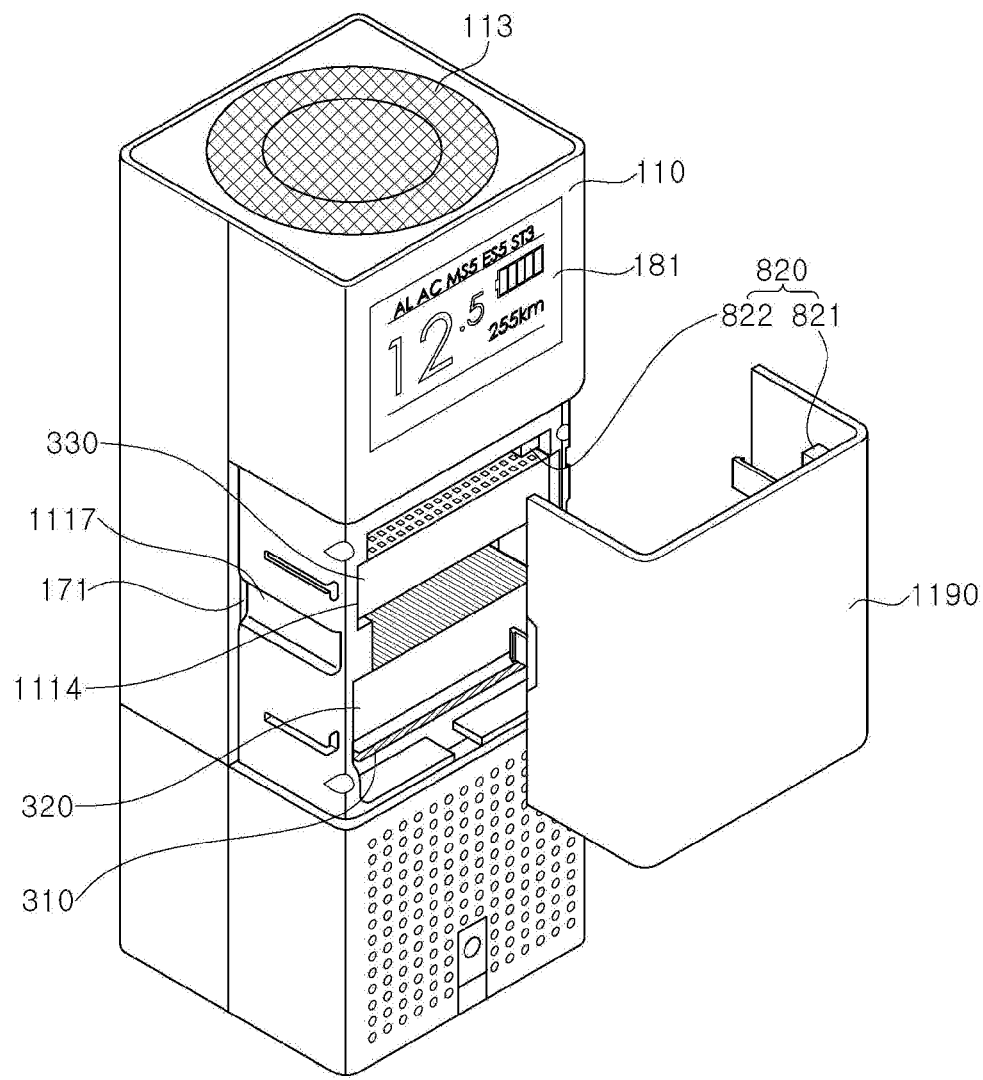
FIG. 21 is a schematic view of an air purifier according to a seventeenth exemplary embodiment.

FIG. 21 is a schematic view of an air purifier according to a seventeenth exemplary embodiment.

In descriptions of an air purifier 1700 according to the seventeenth exemplary embodiment, repeated description of the same components as those of the air purifiers according to the eleventh to sixteenth exemplary embodiments will be omitted.

Referring to FIG. 21, the air purifier 1700 according to the seventeenth exemplary embodiment includes a door sensor 820.

The door sensor 820 detects whether the door 1190 is open or closed. When the door 1190 is open, the filter replacement portion 1114 of the body 110 is exposed to the outside. When the door 1190 is closed, the door 1190 closely contacts the body 110 to close the filter replacement portion 1114.

For example, the door sensor 820 is a magnetic sensor, and magnet switches 821, 822 may be provided to the door 1190 and the body 110, respectively. When the door 1190 is open, the magnet switches 821, 822 provided to the door 1190 and the body 110 are separated from each other. In addition, when the door 1190 is closed, the magnet switches 821, 822 provided to the door 1190 and the body 110 adjoin each other. The door sensor 820 may detect opening or closing of the door 1190 based on whether the magnet switches 821, 822 adjoin each other.

Although the door sensor 820 is illustrated as a magnetic sensor in the illustrated exemplary embodiment, the type of the door sensor 820 is not limited thereto. According to an exemplary embodiment, the door sensor 820 may be selected from any kind of sensor capable of detecting whether the door 1190 is open or closed.

In addition, according to the illustrated exemplary embodiment, the door sensor 820 may be connected to the power controller 1150 (see FIG. 13). For example, the door sensor 820 may send door-open and door-closed signals to the power controller 1150 (see FIG. 13) depending upon whether the door 1190 is open or closed. The power controller 1150 (see FIG. 13) stops power supply to the light source module 1140 and the fan 180 in response to the door-open signal.

The power controller 1150 (see FIG. 13) starts power supply to the light source module 1140 and the fan 180 in response to the door-closed signal from the door sensor 820.

Alternatively, the power controller 1150 (see FIG. 13) may start power supply to the light source module 1140 and the fan 180 only in response to both a power signal from the power source 1130 and the door-closed signal from the door sensor 820.

According to the illustrated exemplary embodiment, the door sensor 820 may send the door-open signal and the door-closed signal to the output unit 181. The output unit 181 may output a door-open alarm and a door-closed alarm in response to the door-open signal and the door-closed signal.

Figure 22:
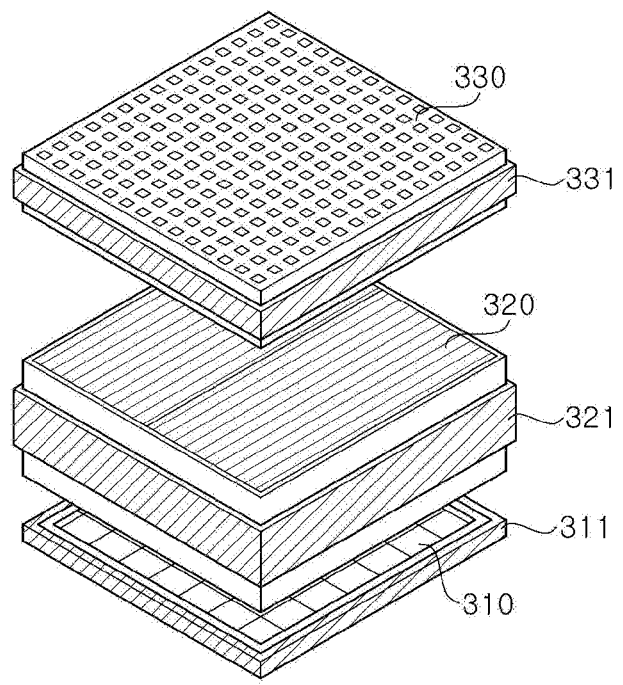
FIG. 22 is a schematic view of an air purifier according to an eighteenth exemplary embodiment.

FIG. 22 is a schematic view of an air purifier according to an eighteenth exemplary embodiment.

An air purifier 1800 according to the eighteenth exemplary embodiment has the same components excluding first to third filters 310 to 330 as those of the air purifiers according to the eleventh to seventeenth exemplary embodiments. Accordingly, illustration of the other components excluding the first to third filters 310 to 330 is omitted. Descriptions of the components omitted below are described above with reference to the air purifiers according to the eleventh to seventeenth exemplary embodiments.

Referring to FIG. 22, the first to third filters 310 to 330 are provided with first to third resilient frames 311 to 331, respectively.

The first to third resilient frames 311 to 331 are formed of a resilient material. For example, the first to third resilient frames 311 to 331 may be formed of rubber or a porous material, such as a sponge.

The first resilient frame 311 is mounted on the first filter 310 to surround an outer surface of the first filter 310. The second resilient frame 321 is mounted on the second filter 320 to surround an outer surface of the second filter 320. The third resilient frame 331 is mounted on the third filter 330 to surround an outer surface of the third filter 330.

The first to third resilient frames 311 to 331 enable easy detachment or attachment of the first to third filters 310 to 330 to the interior of the body 110. The third filter 330 acting as a photocatalytic filter is formed of a rigid material, such as a ceramic material, and does not allow easy insertion into the body 110. However, according to the illustrated exemplary embodiment, although the third filter 330 is rigid, the third resilient frame 331 is compressed by external force to allow the third filter 330 to be easily inserted into the body 110 due to elasticity of the third resilient frame 331.

In this manner, the first filter 310 and the second filter 320 can also be easily inserted into the body 110 by the first resilient frame 311 and the second resilient frame 321 mounted thereon.

Although the first to third resilient frames 311 to 331 are illustrated as being mounted on the first to third filters 310 to 330, respectively, the inventive concepts are not limited thereto. For example, when the filters are formed to have elasticity, the resilient frames may be omitted. More particularly, when the first filter 310 and the second filter 320 have elasticity, the third resilient frame 331 may be provided only to the third filter 330.

Figure 23:
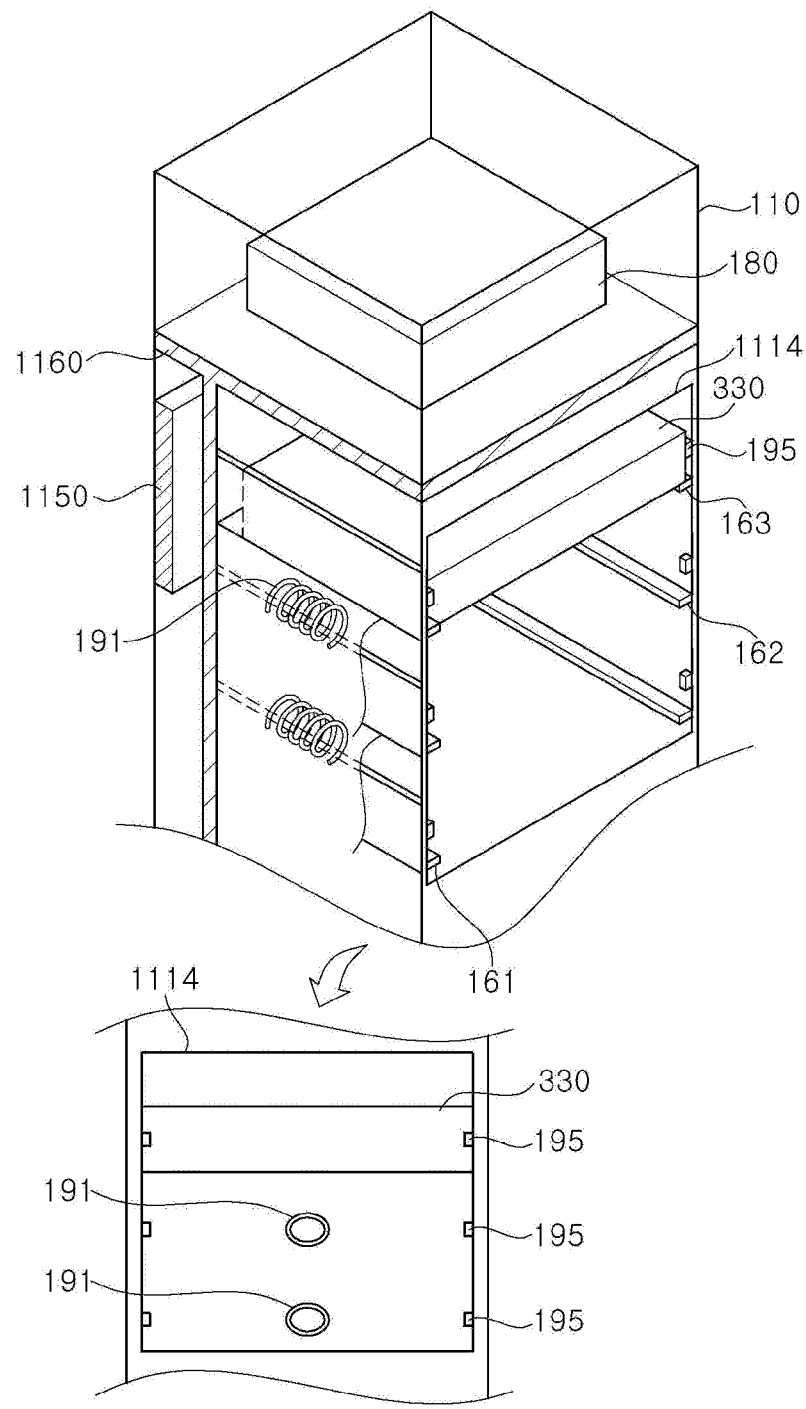
FIG. 23 is a schematic view of an air purifier according to a nineteenth exemplary embodiment.

FIG. 23 is a schematic view of an air purifier according to a nineteenth exemplary embodiment.

In descriptions of an air purifier 1900 according to the nineteenth exemplary embodiment, repeated description of the same components as those of the air purifiers according to the eleventh to eighteenth exemplary embodiments will be omitted.

Referring to FIG. 23, the air purifier 1900 is provided with springs 191 for easy detachment and attachment of the first to third filters 310 to 330. In FIG. 23, the first filter 310 and the second filter 320 shown in FIGS. 13 to 22 are not shown. According to the illustrated exemplary embodiment, each of the springs 191 is provided to a portion of the cover 1160 where each of the first to third filters 310 to 330 is mounted.

In addition, the body 110 is provided with stoppers 195. The stoppers 195 protrude from both sides of the filter replacement portion 1114, such that the first to third filters 310 to 330 are placed inside the body 110. The stoppers 195 are formed at an inlet side of the filter replacement portion 1114 of the body 110. For example, the stoppers 195 may be formed on the first to third filter securing portions 161 to 163 at the inlet side of the filter replacement portion 1114. The first to third filters 310 to 330 are inserted into the body 110 to be disposed at predetermined locations inside the body 110 while compressing the spring 191. When force applied to the spring 191 is removed, the stoppers 195 prevent the first to third filters 310 to 330 from escaping from the body 110 by elastic force of the spring 191. Further, the first to third filters 310 to 330 may be secured at predetermined locations by elastic force of the spring 191 and the stoppers 195. In addition, the spring 191 and the stoppers 195 may be formed to allow mounting of only at least one of the first to third filters 310 to 330.

For example, the first filter 310 and the second filter 320 may be formed of an elastic material and the third filter 330 may be formed of an inelastic material. Here, the first filter 310 and the second filter 320 are inserted into the first filter securing portion 161 and the second filter securing portion 162 to be secured inside the body 110 by elastic force thereof, as in the eleventh exemplary embodiment. The third filter 330 having no elasticity may be secured inside the body 110 by the spring 191 and the stoppers 195. In this manner, the locations and the number of the springs 191 and the stoppers 195 may be variously modified, as needed.

Figure 24:
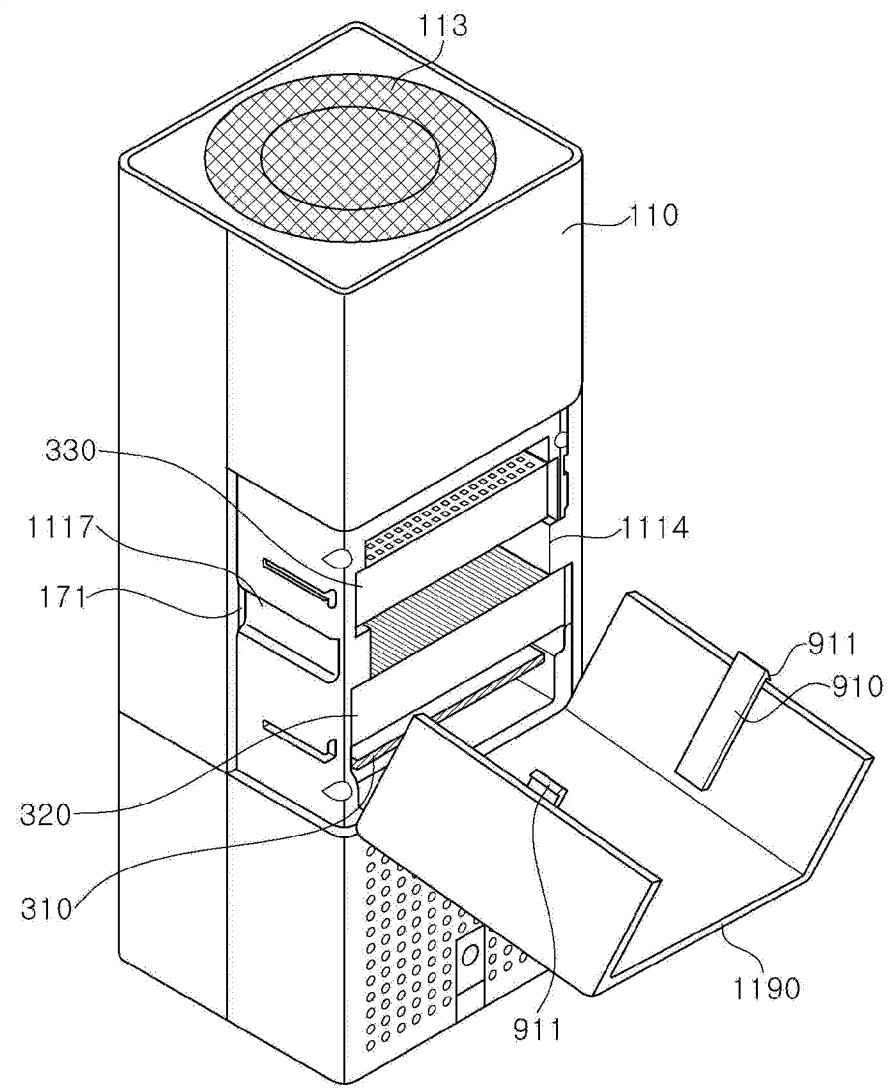
FIG. 24 and FIG. 25 are schematic views of air purifiers according to twentieth and twenty first exemplary embodiments.
Figure 25:
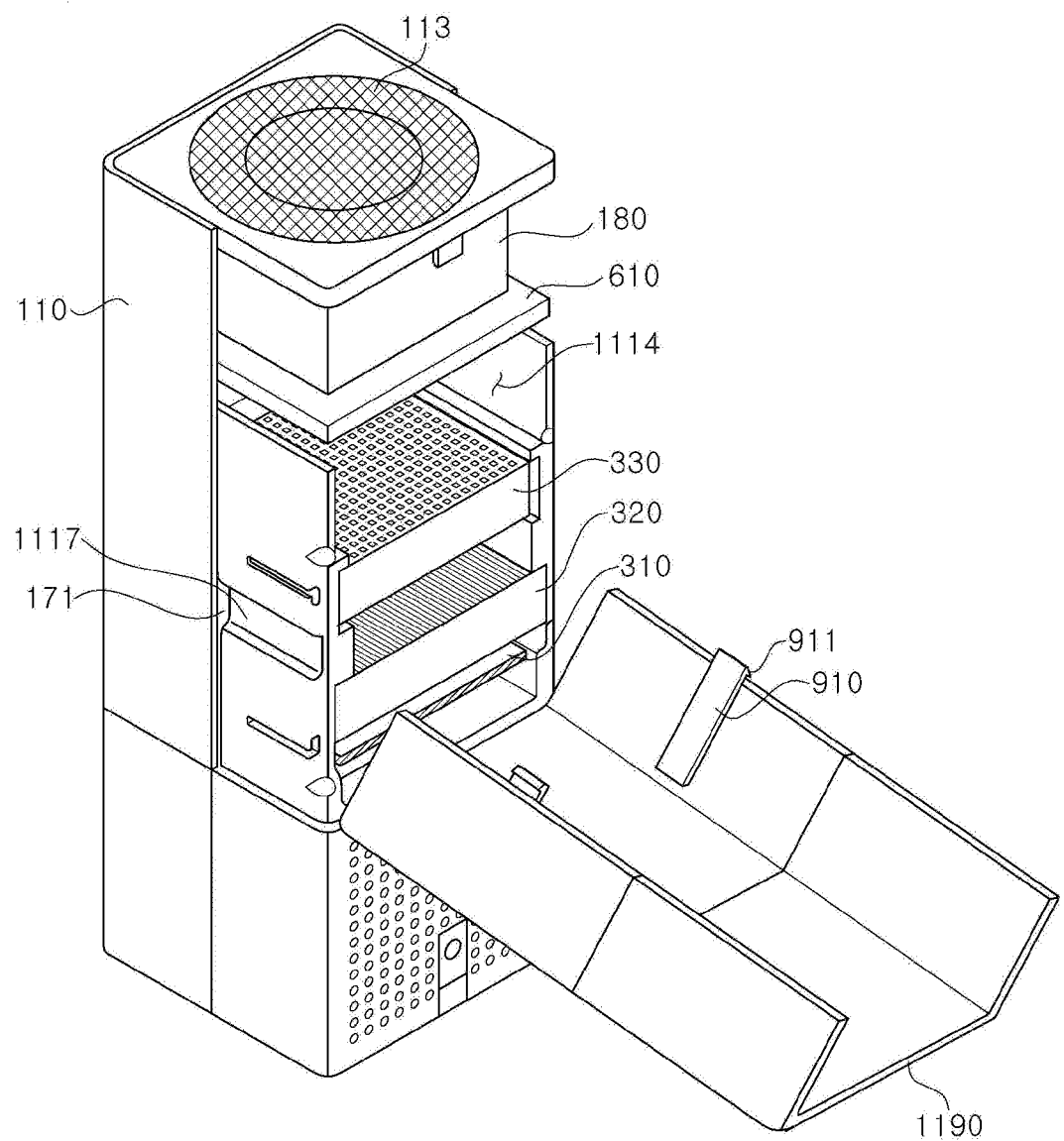

FIG. 24 and FIG. 25 are schematic views of air purifiers according to twentieth and twenty first exemplary embodiments.

In descriptions of air purifiers 2000, 2100 according to the twentieth and twenty first exemplary embodiments, repeated descriptions of the same components as those of the air purifiers according to the eleventh to twentieth exemplary embodiments will be omitted.

According to the illustrated exemplary embodiment, the door 1190 is formed to surround both sides of the body 110 and the filter replacement portion 1114. With this structure, the door 1190 is opened or closed, with a portion of the door 1190 connected to the body 110. Referring to FIG. 24 and FIG. 25, a lower end of the door 1190 is connected to the body 110. Accordingly, with the lower end of the door 1190 secured to the body 110, the door 1190 is opened or closed by detaching or attaching an upper end and a side surface of the door 1190 to the body 110.

FIG. 24 shows the filter replacement portion 1114 formed to expose only the first to third filters 310 to 330, and FIG. 25 shows the filter replacement portion 1114 formed to expose not only the first to third filters 310 to 330 but also the fan 180. The structure of the door 1190 may be changed depending upon the size of the filter replacement portion 1114 so as to open or close the filter replacement portion 1114.

The door 1190 is formed at both sides thereof with door guides 910 extending in a direction of being coupled to the body 110 on the side surfaces of the door 1190. Each of the door guides 910 is formed at one end thereof with a door securing portion 911 protruding outward from the door guide 910.

The body 110 is formed with door guide grooves 1171 on an outer wall thereof so as to correspond to the door guides 910, respectively. Each of the door guide grooves 1171 of the body 110 is formed at one end thereof with a door securing groove 171.

The door securing groove 171 is covered by the outer wall of the body 110 excluding an inlet thereof connected to the door guide groove 1171. A door securing portion 911 is formed to pass through a gap between the outer wall of the body 110 and the inlet of the door securing groove 171.

The door securing groove 171 is formed to allow the door securing portion 911 to be inserted into the door securing groove 171 when force is applied to both sides of the door 1190 and to allow the door securing portion 911 to be caught by the outer wall of the body 110 upon removal of force therefrom.

That is, when the door 1190 is coupled to the body 110, the door guides 910 are inserted into the door guide grooves 1171, and the door securing portions 911 are inserted into the door securing grooves 171. Then, the door securing portions 911 are secured to the door securing grooves 171 by being blocked by the outer wall of the body 110 due to the protruding structure thereof. As a result, the door 1190 is in a closed state to cover the filter replacement portion 1114.

When the door 1190 is in the closed state, the door securing portions 911 are forced to pass through a gap between the outer wall of the body 110 and the door securing grooves 171 by applying force to both sides of the door 1190 such that the door 1190 can be opened.

The door securing portions 911 may be further formed on the inner wall of the door 1190 at an upper portion thereof, and the door securing grooves 171 may also be further formed on the body 110 at locations corresponding to the door securing portions 911.

Referring to FIG. 25, the body 110 is formed such that the side surfaces of the body 110 surround the periphery of the upper surface of the body 110 having the discharge port 113 formed thereon. That is, the periphery of the upper surface of the body 110 is surrounded by the side surfaces thereof. When the door 1190 is closed, an upper portion of the door 1190 also surrounds the periphery of the upper surface of the body 110. For example, when the upper surface of the body 110 is disposed on the side surfaces thereof to be secured thereby, the upper portion of the door 1190 is also disposed under the upper surface of the body 110 when the door 1190 is closed. In addition, an upper end of the door 1190 is brought into close contact with the inner surface of the upper surface of the body 110 and moves along a curved line upon opening and closing the door 1190. Accordingly, when the door 1190 is opened or closed, friction occurs between the upper end of the door 1190 and the inner wall of the upper surface of the body 110. As a result, the door 1190 cannot be easily opened or closed and the body 110 can be damaged.

However, when the periphery of the upper surface of the body 110 is surrounded by the side surfaces of the body 110 as in the illustrated exemplary embodiment, friction does not occur between the door 1190 and the upper surface of the body 110, and the body 110 can be prevented from being damaged.

Figure 26:
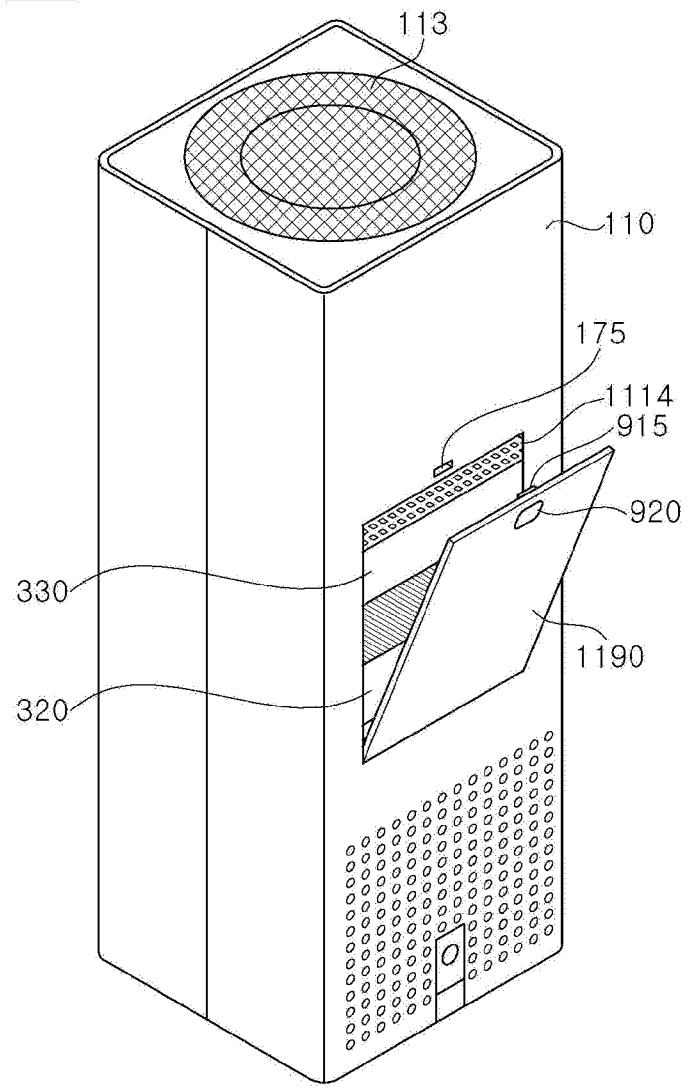
FIG. 26 is a schematic view of an air purifier according to a twenty second exemplary embodiment.

FIG. 26 is a schematic view of an air purifier according to a twenty second exemplary embodiment.

In descriptions of an air purifier 2200 according to the twenty second exemplary embodiment, repeated descriptions of the same components as those of the air purifiers according to the eleventh to twenty first exemplary embodiments will be omitted.

According to the illustrated exemplary embodiment, the door 1190 is formed to cover a surface of the body 110 on which the filter replacement portion 1114 is formed.

In the twenty second exemplary embodiment, the door 1190 is formed to cover one surface of the body on which the filter replacement portion 1114 is formed.

According to the illustrated exemplary embodiment, an upper outer wall of the door 1190 is formed with a door button 920. In addition, the door 1190 is formed with a door securing portion 915 on an upper inner wall thereof, and the body 110 is formed with a door securing groove 175 at a location thereof corresponding to the door securing portion 915.

The door securing portion 915 is physically or electrically connected to the door button 920. Accordingly, when the door button 920 is pushed or touched, the door securing portion 915 may protrude outwards from the door 1190 or may be inserted into the door 1190.

For example, with the door securing portion 915 inserted into the door 1190, the door 1190 is brought into close contact with the body 110. When the door button 920 is operated in this state, the door securing portion 915 protrudes outwards from the door 1190, the door securing portion 915 is inserted into the door securing groove 175 of the body 110. As a result, the door 1190 is in a closed state wherein the door 1190 is secured to the body 110. In addition, when the door button 920 is operated with the door 1190 secured to the body 110, the door securing portion 915 is inserted into the door 1190. As a result, the door 1190 is opened to be detached from the body 110.

Figure 27:
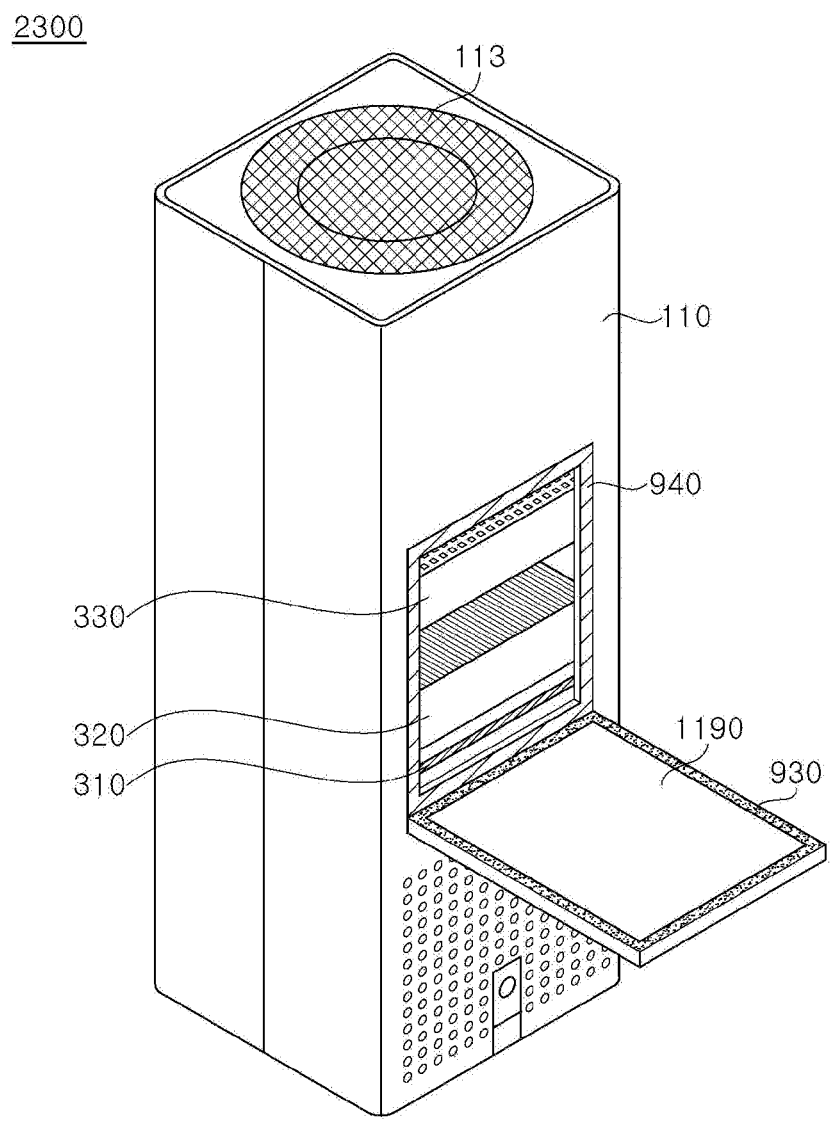
FIG. 27 is a schematic view of an air purifier according to a twenty third exemplary embodiment.

FIG. 27 is a schematic view of an air purifier according to a twenty third exemplary embodiment.

In descriptions of an air purifier 2300 according to the twenty third exemplary embodiment, repeated descriptions of the same components as those of the air purifiers according to the eleventh to twenty second exemplary embodiments will be omitted.

Referring to FIG. 27, the door 1190 is formed to cover only one surface of the body 110 as shown in FIG. 26.

According to the illustrated exemplary embodiment, a portion of the door 1190 is formed with a magnetic component. For example, a gasket 930 may be mounted along the periphery of the door 1190. Further, the door 1190 is provided with a sensor or a switch.

The body 110 is provided with an electromagnet 940. The electromagnet 940 is mounted on a portion of the body 110 contacting the gasket 930 of the door 1190.

For example, when the door 1190 is brought into close contact with the body 110, attractive force is generated between the gasket 930 of the door 1190 and the electromagnet 940 of the body 110. As a result, the door 1190 is secured to the body 110 in a closely contacting state by the attractive force therebetween, whereby the door 1190 is closed. When a signal is applied to the sensor or the switch by applying force to the door 1190 brought into close contact with the body 110, electric current is supplied to the electromagnet 940. Accordingly, the electromagnet 940 exhibits polarity, thereby generating repulsive force between the electromagnet 940 and the gasket 930. As a result, the door 1190 and the body 110 are pushed away from each other by the repulsive force, whereby the door 1190 is opened.

With the electromagnet 940 and the gasket 930, the air purifier 2300 enables easy opening and closing of the door 1190.

Herein, various structures for opening and closing the door 1190 through the structures of the door 1190 and the body 110 are described. However, the inventive concepts are not limited to the aforementioned structures for opening and closing the door 1190. The structure for opening and closing the door 1190 may be variously modified as needed.

Figure 28:
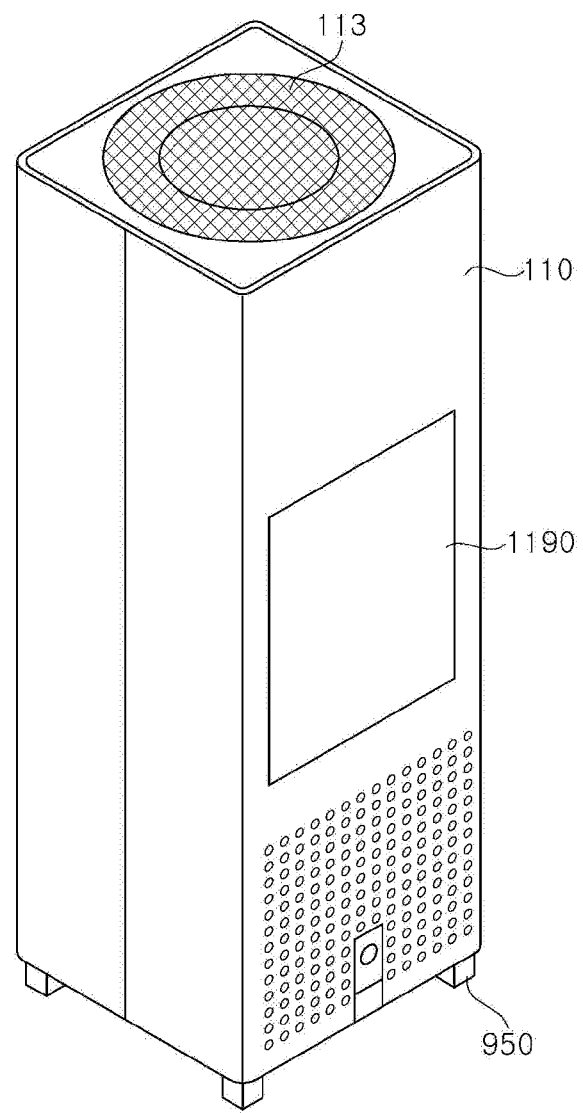
FIG. 28 is a schematic view of an air purifier according to a twenty fourth exemplary embodiment.

FIG. 28 is a schematic view of an air purifier according to a twenty fourth exemplary embodiment.

In descriptions of an air purifier 2400 according to the twenty fourth exemplary embodiment, repeated descriptions of the same components as those of the air purifiers according to the eleventh to twenty fourth exemplary embodiments will be omitted.

Referring to FIG. 28, the air purifier 2400 may include a support 950. The support 950 is formed on one surface of the outer wall of the body 110.

The support 950 is formed to separate a lower surface of the body 110 of the air purifier 2400 from the floor of an installation space of the air purifier 2400. Accordingly, the power source 1130 may be formed at any location of the body 110. For example, even when the power source 1130 is formed on the lower surface of the body 110, since the power source 1130 is separated from the floor of the installation space of the air purifier 2400, the power source 1130 can be prevented from malfunctioning due to contact with the floor of the installation space.

In addition, the support 950 may provide an increased degree of design freedom for the suction port. For example, since the lower surface of the body 110 is spaced apart from the floor of the installation space by the support 950, the suction port may also be formed on the lower surface of the body 110. When the suction port is formed on the lower surface of the body 110, an air passage is formed from the suction port to the first to third filters, the fan and the discharge port in one direction. With the air passage formed in one direction, air loss inside the air purifier 2400 can be reduced, thereby improving air purification efficiency.

Although some exemplary embodiments have been described herein, it should be understood that these exemplary embodiments are provided for illustration only and are not to be construed in any way as limiting the exemplary embodiment of the disclosure, and that various modifications, changes, alterations, and equivalent embodiments can be made by those skilled in the art without departing from the spirit and scope of the invention.

The invention claimed is:

1. An air purifier comprising:
   a body including a suction port and a discharge port disposed on two opposing surfaces thereof, the body having an inner space through which air flows from the suction port to the discharge port;
   a fan disposed in the inner space of the body, the fan having a side surface separated from an inner wall of the body;
   at least one light source module disposed in the inner space of the body, the at least one light source module comprising at least one UV light source;
   a power controller mounted on the inner wall of the body and physically or electrically connected to a power source to supply electric power to the at least one light source module;
   a cover mounted on the inner wall of the body and formed to cover the power controller; and
   at least one filter disposed in the inner space of the body,
   wherein the cover includes a tilted air flow guide facet formed at a first side thereof to guide air suctioned through the suction port toward the at least one filter.

2. The air purifier according to claim 1, wherein the body further includes filter securing portions disposed on both sides of the inner wall thereof to receive both sides of the at least one filter inserted thereinto.

3. The air purifier according to claim 1, wherein the cover further includes a fan securing portion disposed at a second side thereof different from the first side to place the fan in a direction parallel with the discharge port.

4. The air purifier according to claim 1, wherein the cover further comprises a light source module support that supports the at least one light source module and separating the at least one light source module from the cover.

5. The air purifier according to claim 1, wherein the body further includes light source module grooves disposed on the inner wall thereof to receive both sides of the at least one light source module inserted thereinto.

6. The air purifier according to claim 1, wherein the at least one filter comprises at least one of a photocatalytic filter and a HEPA filter.

7. The air purifier according to claim 6, wherein the at least one light source module emits UV light toward the photocatalytic filter, the HEPA filter, or both of the photocatalytic filter and the HEPA filter.

8. The air purifier according to claim 1, wherein the tilted air flow guide facet has a gradually increasing height from the suction port toward the at least one filter.

9. The air purifier according to claim 1, further comprising a resilient frame surrounding an outer surface of the at least one filter.

* * * * *